(12) United States Patent
Kopelman et al.

(10) Patent No.: US 9,510,757 B2
(45) Date of Patent: Dec. 6, 2016

(54) IDENTIFICATION OF AREAS OF INTEREST DURING INTRAORAL SCANS

(71) Applicant: Align Technology, Inc., San Jose, CA (US)

(72) Inventors: Avi Kopelman, Palo Alto, CA (US); Michael Sabina, Campbell, CA (US); Adi Levin, Nes Tziona (IL); Mikhail Minchenkov, Kratovo (RU); Maria Anufrienko, Moscow (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 14/705,788

(22) Filed: May 6, 2015

(65) Prior Publication Data
US 2015/0320320 A1  Nov. 12, 2015

Related U.S. Application Data

(60) Provisional application No. 61/990,004, filed on May 7, 2014.

(51) Int. Cl.
*G06K 9/00* (2006.01)
*A61B 5/00* (2006.01)
*A61B 6/03* (2006.01)
(Continued)

(52) U.S. Cl.
CPC ........... *A61B 5/0088* (2013.01); *A61B 5/4547* (2013.01); *A61B 5/4552* (2013.01); *A61B 5/486* (2013.01); *A61B 5/7264* (2013.01); *A61B 6/032* (2013.01); *A61B 6/14* (2013.01); *A61B 6/145* (2013.01); *A61B 6/5241* (2013.01); *A61C 7/002* (2013.01); *A61C 9/0053* (2013.01); *A61C 13/0004* (2013.01); *A61C 13/34* (2013.01); *G06T 7/0065* (2013.01); *G06T 7/0071* (2013.01); *A61B 6/469* (2013.01);
(Continued)

(58) Field of Classification Search
CPC .......... G06T 2207/10016; G06T 2207/30036; G06T 7/0065; G06T 7/0071; A61B 2576/02; A61B 5/0088; A61B 5/4547; A61B 5/4552; A61B 6/14; A61C 13/0004; A61C 13/34; A61C 7/002; A61C 9/0053
See application file for complete search history.

(56) References Cited

U.S. PATENT DOCUMENTS 7,286,954 B2  10/2007  Kopelman et al.
7,862,336 B2  1/2011  Kopelman et al.
(Continued)

FOREIGN PATENT DOCUMENTS

EP  1662414 A2  5/2006
WO  2007084647 A2  7/2007

OTHER PUBLICATIONS

International Search Report and Written Opinion for PCT Application No. PCT/IB2015/000653 mailed Sep. 14, 2015.

*Primary Examiner* — Phuoc Tran
(74) *Attorney, Agent, or Firm* — Lowenstein Sandler LLP

(57) ABSTRACT

During an intraoral scan session, a processing device receives a first intraoral image of a dental site and identifies a candidate intraoral area of interest from the first intraoral image. The processing device receives a second intraoral image of the dental site and verifies the first candidate intraoral area of interest as an intraoral area of interest based on comparison of the second intraoral image to the first intraoral image. The processing device then provides an indication of the intraoral area of interest during the intraoral scan session.

21 Claims, 12 Drawing Sheets

(51) Int. Cl.
*A61B 6/14* (2006.01)
*A61C 7/00* (2006.01)
*A61C 13/00* (2006.01)
*A61C 13/34* (2006.01)
*A61C 9/00* (2006.01)
*G06T 7/00* (2006.01)
*A61B 6/00* (2006.01)

(52) U.S. Cl.
CPC . *A61B 2576/02* (2013.01); *G06T 2207/10016* (2013.01); *G06T 2207/30036* (2013.01)

(56) References Cited

U.S. PATENT DOCUMENTS

| | | |
|---|---|---|
| 2005/0283065 A1 | 12/2005 | Babayoff |
| 2013/0330685 A1* | 12/2013 | Lahelma .............. A61C 9/0006 433/29 |
| 2014/0213888 A1* | 7/2014 | Idiyatullin ....... G01R 33/34084 600/422 |
| 2014/0272772 A1* | 9/2014 | Andreiko ............... A61C 7/002 433/29 |

* cited by examiner

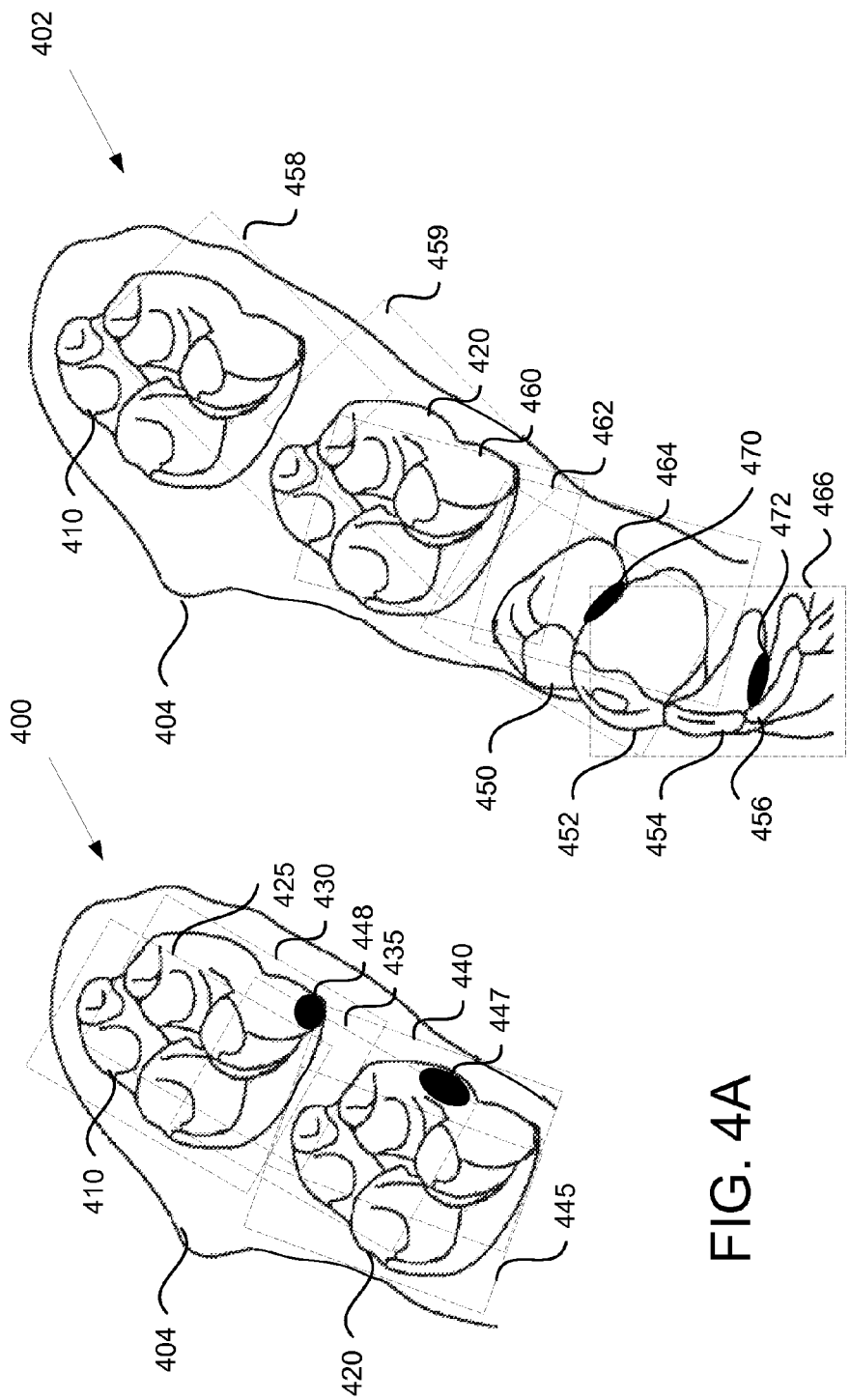

IDENTIFICATION OF AREAS OF INTEREST DURING INTRAORAL SCANS

RELATED APPLICATIONS

This patent application claims the benefit under 35 U.S.C. §119(e) of U.S. Provisional Application No. 61/990,004, filed May 7, 2014, which is herein incorporated by reference.

TECHNICAL FIELD

Embodiments of the present invention relate to the field of intraoral scanning and, in particular, to a system and method for improving the results of intraoral scanning.

BACKGROUND

In prosthodontic procedures designed to implant a dental prosthesis in the oral cavity, the dental site at which the prosthesis is to be implanted in many cases should be measured accurately and studied carefully, so that a prosthesis such as a crown, denture or bridge, for example, can be properly designed and dimensioned to fit in place. A good fit enables mechanical stresses to be properly transmitted between the prosthesis and the jaw, and to prevent infection of the gums via the interface between the prosthesis and the dental site, for example.

Some procedures also call for removable prosthetics to be fabricated to replace one or more missing teeth, such as a partial or full denture, in which case the surface contours of the areas where the teeth are missing need to be reproduced accurately so that the resulting prosthetic fits over the edentulous region with even pressure on the soft tissues.

In some practices, the dental site is prepared by a dental practitioner, and a positive physical model of the dental site is constructed using known methods. Alternatively, the dental site may be scanned to provide 3D data of the dental site. In either case, the virtual or real model of the dental site is sent to the dental lab, which manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry has to be altered to avoid the collision, which may result in the coping design being less optimal. Further, if the area of the preparation containing a finish line lacks definition, it may not be possible to properly determine the finish line and thus the lower edge of the coping may not be properly designed. Indeed, in some circumstances, the model is rejected and the dental practitioner then re-scans the dental site, or reworks the preparation, so that a suitable prosthesis may be produced.

In orthodontic procedures it can be important to provide a model of one or both jaws. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a three-dimensional (3D) model of a dental site in the oral cavity is an initial procedure that is performed. When the 3D model is a virtual model, the more complete and accurate the scans of the dental site are, the higher the quality of the virtual model, and thus the greater the ability to design an optimal prosthesis or orthodontic treatment appliance(s).

BRIEF DESCRIPTION OF THE DRAWINGS

The present invention is illustrated by way of example, and not by way of limitation, in the figures of the accompanying drawings.

FIG. 4A illustrates a portion of an example dental arch during an intraoral scan session.

FIG. 4B illustrates the example dental arch of FIG. 4A during the intraoral scan session after the generation of further intraoral images.

DETAILED DESCRIPTION

Described herein is a method and apparatus for improving the quality of scans, such as intraoral scans taken of dental sites for patients. During a scan session, a user (e.g., a dental practitioner) of a scanner may generate multiple different images (also referred to as scans) of a dental site, model of a dental site, or other object. The images may be discrete images (e.g., point-and-shoot images) or frames from a video (e.g., a continuous scan). These images may not capture all of the areas of the dental site and/or there may be areas for which there is conflicting data between images. In embodiments described herein, such missing areas and/or conflicting areas may be identified as areas of interest. This identification may be performed during a scan session. Accordingly, shortly after the user of the scanner has generated one or more images, the user may be notified of areas of interest that should be rescanned. The user may then rescan the areas of interest during the scan session. This can facilitate quick and accurate scan sessions.

Additionally, indications or indicators of areas of interest can be generated during a scan session or after the scan session is complete. These indications may indicate classifications associated with areas of interest, a severity of the areas of interest, a size of the areas of interest, and additional information. The indications may be visible in views of the dental site or other scanned object in which the actual areas of interest are hidden. This can ensure that the user will be made aware of the areas of interest regardless of a current view.

Embodiments described herein are discussed with reference to intraoral scanners, intraoral images, intraoral scan sessions, and so forth. However, it should be understood that embodiments also apply to other types of scanners than intraoral scanners. Embodiments may apply to any type of scanner that takes multiple images and stitches these images together to form a combined image or virtual model. For example, embodiments may apply to desktop model scanners, computed tomography (CT scanners, and so forth. Additionally, it should be understood that the intraoral scanners or other scanners may be used to scan objects other than dental sites in an oral cavity. For example, embodiments may apply to scans performed on physical models of a dental site or any other object. Accordingly, embodiments describing intraoral images should be understood as being generally applicable to any types of images generated by a scanner, embodiments describing intraoral scan sessions should be understood as being applicable to scan sessions for any type of object, and embodiments describing intraoral scanners should be understood as being generally applicable to many types of scanners.

Figure 1:
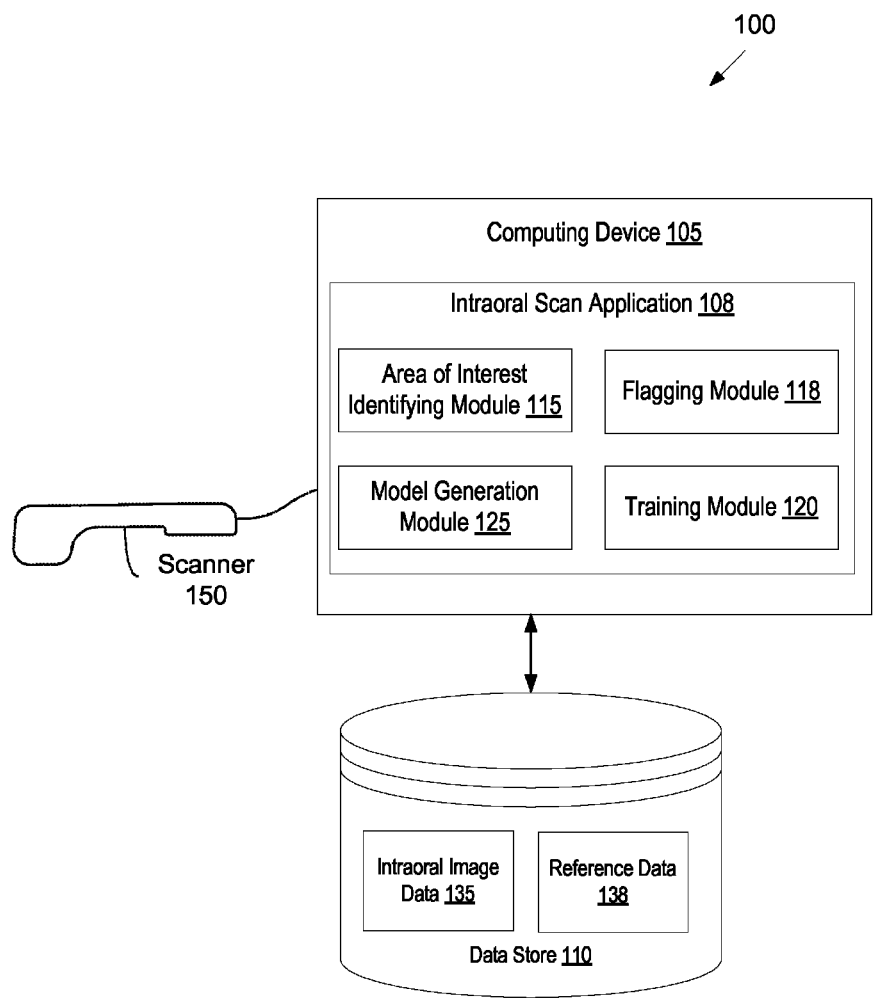
FIG. 1 illustrates one embodiment of a system for performing intraoral scanning and generating a virtual three dimensional model of a dental site.

FIG. 1 illustrates one embodiment of a system 100 for performing intraoral scanning and/or generating a virtual three dimensional model of a dental site. In one embodiment, system 100 carries out one or more operations of below described in methods 200, 250, 300, 340 and/or 370. System 100 includes a computing device 105 that may be coupled to a scanner 150 and/or a data store 110.

Computing device 105 may include a processing device, memory, secondary storage, one or more input devices (e.g., such as a keyboard, mouse, tablet, and so on), one or more output devices (e.g., a display, a printer, etc), and/or other hardware components. Computing device 105 may be connected to a data store 110 either directly or via a network. The network may be a local area network (LAN), a public wide area network (WAN) (e.g., the Internet), a private WAN (e.g., an intranet), or a combination thereof. The computing device 105 may be integrated into the scanner 150 in some embodiments to improve performance and mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

In some embodiments, a scanner 150 for obtaining three-dimensional (3D) data of a dental site in a patients oral cavity is operatively connected to the computing device 105. Scanner 150 may include a probe (e.g., a hand held probe) for optically capturing three dimensional structures (e.g., by confocal focusing of an array of light beams). One example of such a scanner 150 is the iTero® intraoral digital scanner manufactured by Align Technology, Inc. Other examples of intraoral scanners include the 1M™ True Definition Scanner and the Apollo DI intraoral scanner and CEREC AC intraoral scanner manufactured by Sirona®.

The scanner 150 may be used to perform an intraoral scan of a patient's oral cavity. An intraoral scan application 108 running on computing device 105 may communicate with the scanner 150 to effectuate the intraoral scan. A result of the intraoral scan may be a sequence of intraoral images that have been discretely generated (e.g., by pressing on a "generate image" button of the scanner for each image). Alternatively, a result of the intraoral scan may be one or more videos of the patients oral cavity. An operator may start recording the video with the scanner 150 at a first position in the oral cavity, move the scanner 150 within the oral cavity to a second position while the video is being taken, and then stop recording the video. In some embodiments, recording may start automatically as the scanner identifies either teeth. The scanner 150 may transmit the discrete intraoral images or intraoral video (referred to collectively as intraoral image data 135) to the computing device 105. Computing device 105 may store the image data 135 in data store 110. Alternatively, scanner 150 may be connected to another system that stores the image data in data store 110. In such an embodiment, scanner 150 may not be connected to computing device 105.

According to an example, a user (e.g., a practitioner) may subject a patient to intraoral scanning. In doing so, the user may apply scanner 150 to one or more patient intraoral locations. The scanning may be divided into one or more segments. As an example the segments may include a lower buccal region of the patient, a lower lingual region of the patient, a upper buccal region of the patient, an upper lingual region of the patient, one or more preparation teeth of the patient (e.g., teeth of the patient to which a dental device such as a crown or an orthodontic alignment device will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with scan being directed towards an interface area of the patient's upper and lower teeth). Via such scanner application, the scanner 150 may provide image data (also referred to as scan data) 135 to computing device 105. The image data 135 may include 2D intraoral images and/or 3D intraoral images. Such images may be provided from the scanner to the computing device 105 in the form of one or more points (e.g., one or more pixels and/or groups of pixels). For instance, the scanner 150 may provide such a 3D image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring abutment teeth and the opposing arch and dentition. Thus, the dental practitioner may input the identity of a procedure to be performed into intraoral scan application 108. For this purpose, the dental practitioner may choose the procedure from a number of preset options on a drop-down menu or the like, from icons or via any other suitable graphical input interface. Alternatively, the identity of the procedure may be input in any other suitable way, for example by means of preset code, notation or any other suitable manner, intraoral scan application 108 having been suitably programmed to recognize the choice made by the user.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances.

A type of scanner to be used may also be input into intraoral scan application 108, typically by a dental practitioner choosing one among a plurality of options. If the scanner 150 that is being used is not recognizable by intraoral scan application 108, it may nevertheless be possible to input operating parameters of the scanner thereto instead. For example, the optimal spacing between a head of the scanner and scanned surface can be provided, as well as the capture area (and shape thereof) of the dental surface capable of being scanned at this distance. Alternatively, other suitable scanning parameters may be provided.

Intraoral scan application 108 may identify spatial relationships that are suitable for scanning the dental site so that complete and accurate image data may be obtained for the procedure in question. Intraoral scan application 108 may establish an optimal manner for scanning a target area of the dental site.

Intraoral scan application 108 may identify or determine a scanning protocol by relating the type of scanner, resolution thereof, capture area at an optimal spacing between the scanner head and the dental surface to the target area, etc. For a point-and-shoot scanning mode, the scanning protocol comprises a series of scanning stations spatially associated with the dental surfaces of the target area. Preferably, overlapping of the images or scans capable of being obtained at adjacent scanning stations is designed into the scanning protocol to enable accurate image registration, so that intraoral images can be stitched together to provide a composite 3D virtual model. For a continuous scanning mode (video scan), scanning stations may not be identified. Instead, a practitioner may activate the scanner and proceed to move the scanner within the oral cavity to capture a video of the target area from multiple different viewpoints.

In one embodiment, intraoral scan application 108 includes an area of interest (AOI) identifying module 115, a flagging module 118 and a model generation module 125. Alternatively, the operations of one or more of the AOI identifying module 115, flagging module 118 and/or model generation module 125 may be combined into a single module and/or divided into multiple modules.

AOI identifying module 115 is responsible for identifying areas of interest (AOIs) from intraoral scan data (e.g., intraoral images) and/or virtual 3D models generated from intraoral scan data. Such areas of interest may include voids (e.g., areas for which scan data is missing), areas of conflict or flawed scan data (e.g., areas for which overlapping surfaces of multiple intraoral images fail to match), areas indicative of foreign objects (e.g., studs, bridges, etc.), areas indicative of tooth wear, areas indicative of tooth decay, areas indicative of receding gums, unclear gum line, unclear patient bite, unclear margin line (e.g., margin line of one or more preparation teeth), and so forth. An identified void may be a void in a surface of an image. Examples of surface conflict include double incisor edge and/or other physiologically unlikely tooth edge, and/or bite line shift. The AOI identifying module 115 may, in identifying an AOI, analyze patient image data 135 (e.g., 3D image point clouds) and/or one or more virtual 3D models of the patient alone and/or relative to reference data 138. The analysis may involve direct analysis (e.g., pixel-based and/or other point-based analysis), the application of machine learning, and/or the application of image recognition. Such reference data 138 may include past data regarding the at-hand patient (e.g., intraoral images and/or virtual 3D models), pooled patient data, and/or pedagogical patient data, some or all of which may be stored in data store 110.

The data regarding the at-hand patient may include X-rays, 2D intraoral images, 3D intraoral images, 2D models, and/or virtual 3D models corresponding to the patient visit during which the scanning occurs. The data regarding the at-hand patient may additionally include past X-rays, 2D intraoral images, 3D intraoral images, 2D models, and/or virtual 3D models of the patient (e.g., corresponding to past visits of the patient and/or to dental records of the patient).

The pooled patient data may include X-rays, 2D intraoral images, 3D intraoral images, 2D models, and/or virtual 3D models regarding a multitude of patients. Such a multitude of patients may or may not include the at-hand patient. The pooled patient data may be anonymized and/or employed in compliance with regional medical record privacy regulations (e.g., the Health Insurance Portability and Accountability Act (HIPAA)). The pooled patient data may include data corresponding to scanning of the sort discussed herein and/or other data. The pedagogical patient data may include X-rays, 2D intraoral images, 3D intraoral images, 2D models, virtual 3D models, and/or medical illustrations (e.g., medical illustration drawings and/or other images) employed in educational contexts. The pedagogical patient data may include volunteer data and/or cadaveric data.

AOI identifying module 115 may analyze patient scan data from later in a patient visit during which the scanning occurs (e.g., one or more later-in-the-visit 3D image point clouds and/or one or more later-in-the-visit virtual 3D models of the patient) relative to additional patient scan data in the form of data from earlier in that patient visit (e.g., one or more earlier-in-the-visit 3D image point clouds and/or one or more earlier-in-the-visit virtual 3D models of the patient). AOI identifying module 115 may additionally or alternatively analyze patient scan data relative to reference data in the form of dental record data of the patient and/or data of the patient from prior to the patient visit (e.g., one or more prior-to-the-visit 3D image point clouds and/or one or more prior-to-the-visit virtual 3D models of the patient). AOI identifying module 115 may additionally or alternatively analyze patient scan data relative to pooled patient data and/or pedagogical patient data.

In an example, AOI identifying module 115 may generate a first virtual model of a dental site based on a first scan session of the dental site taken at a first time and later generate a second virtual model of the dental site based on a second scan session of the dental site taken at a second time. The AOI identifying module 115 may then compare the first virtual model to the second virtual model to determine a change in the dental site and identify an AOI to represent the change.

Identifying of areas of interest concerning missing and/or flawed scan data may involve the AOI identifying module 115 performing direct analysis, for instance determining one or more pixels or other points to be missing from patient scan data and/or one or more virtual 3D models of the patient. Identification of areas of interest concerning missing and/or flawed scan data may additionally or alternatively involve employing pooled patient data and/or pedagogical patient data to ascertain patient scan data and/or virtual 3D models as being incomplete (e.g., possessing discontinuities) relative to that which is indicated by the pooled patient data and/or pedagogical patient data.

Flagging module 118 is responsible for determining how to present and/or call out the identified areas of interest. Flagging module 118 may provide indications or indicators regarding scan assistance, diagnostic assistance, and/or foreign object recognition assistance. Areas of interest may be determined, and indicators of the areas of interest may be provided, during and/or after an intraoral scan session. Such indications may be provided prior to and/or without construction of an intraoral virtual 3D model. Alternatively, indications may be provided after constructions of an intraoral virtual 3D model of a dental site.

Examples of the flagging module 118 providing indications regarding scan assistance, diagnostic assistance, and/or foreign object recognition assistance will now be discussed. The flagging module 118 may provide the indications during and/or after an intraoral scan session. The indications may be presented (e.g., via a user interface) to a user (e.g., a practitioner) in connection with and/or apart from one or more depictions of teeth and/or gingivae of a patient (e.g., in connection with one or more X-rays, 2D intraoral images, 3D intraoral images, 2D models, and/or virtual 3D models of the patient). Indication presentation in connection with depictions of patient teeth and/or gingivae may involve the indications being placed so as to correlate an indication with the corresponding portion of the teeth and/or gingivae. As an illustration, a diagnostic assistance indication regarding a broken tooth might be placed so as to identify the broken tooth.

The indications may be provided in the form of flags, markings, contours, text, images, and/or sounds (e.g., in the form of speech). Such a contour may be placed (e.g., via contour fitting) so as to follow an extant tooth contour and/or gingival contour. As an illustration, a contour corresponding to a tooth wear diagnostic assistance indication may be placed so as to follow a contour of the worn tooth. Such a contour may be placed (e.g., via contour extrapolation) with respect to a missing tooth contour and/or gingival contour so as to follow a projected path of the missing contour. As an illustration, a contour corresponding to missing tooth scan data may be placed so as to follow the projected path of the tooth portion which is missing, or a contour corresponding to missing gingival scan data may be placed so as to follow the projected path of the gingival portion which is missing.

In presenting indications (e.g., flags), the flagging module 118 may perform one or more operations to pursue proper indication display. For instance, where indications are displayed in connection with one or more depictions of teeth and/or gingivae (e.g., a corresponding virtual 3D model), such operations may act to display a single indication rather than, say, multiple indications for a single AOI. Additionally, processing logic may select a location in 3D space for indication placement.

Where indications are displayed in connection with a 3D teeth and/or gingiva depiction (e.g., in connection with a virtual 3D model), the flagging module 118 may divide the 3D space into cubes (e.g., voxels corresponding to one or more pixels of the 3D space). The flagging module 118 may then consider the voxels relative to the voxels of determined AOIs and tag voxels so as to indicate the indications (e.g., flags) to which they correspond.

As an illustration, suppose that two indications are to be brought to the attention of the user via flagging: a first indication which regards missing scan data and a second indication which regards a caries. With regard to the missing scan data indication, the flagging module 118 may consider the pixels which correspond to the missing scan data relative to the cubes and tag each cube which encompasses one or more of those pixels. The flagging module 118 may perform likewise with regard to the caries indication.

Where more than one cube is tagged with respect to a given one of the indications, the flagging module 118 may act such that only one of the tagged voxel receives flag placement. Moreover, the flagging module 118 may choose a particular voxel which it determines will provide for ease of viewing by the user. For instance, such choice of a voxel may take into account the totality of indications to be flagged and may endeavor to avoid crowding a single cube with multiple flags where such can be avoided.

In placing indications (e.g., flags) the flagging module 118 may or may not take into account factors other than seeking to avoid crowding. For instance, the flagging module 118 may take into account available lighting, available angle, available zoom, available axes of rotation, and/or other factors corresponding to user viewing of the teeth and/or gingiva depiction (e.g., the virtual 3D model), and may seek indication (e.g., flag) placement which seeks to optimize user viewing in view of these factors).

The flagging module 118 may key the indications (e.g., via color, symbol, icon, size, text, and/or number). The keying of an indication may serve to convey information about that indication. The conveyed information may include classification of an AOI, a size of an AOI and/or an importance rank of an AOI. Accordingly, different flags or indicators may be used to identify different types of AOIs. For example, pink indicators may be used to indicate gingival recession and white indicators may be used to indicate tooth wear. Flagging module 118 may determine a classification, size and/or importance rank of an AOI, and may then determine a color, symbol, icon, text, etc. for an indicator of that AOI based on the classification, size and/or importance rank.

Turning to keying which conveys indication size, the processing logic may, in implementing such size-oriented keying, employ one or more size thresholds. The origin of the thresholds may be set (e.g., by a dental expert) during a configuration operation and/or may be preset. The origin of the thresholds may be set by processing logic which accesses pooled patient data and/or pedagogical patient data correlating size information for foreseeable indications regarding scan assistance (e.g., information regarding sizes of oral-anatomical portions not imaged or poorly imaged due to missing and/or flawed scan data) and degree of success of procedure outcome (e.g., degree of success in orthotic alignment device construction and/or orthotic alignment device patient fit). Larger size may be indicative of greater clinical importance. For example, a large void may impair manufacture of an accurate orthodontic aligner, while a large void may not. As an illustration, three thresholds might be set with respect to areas of missing data and/or caries. Implementation may be such that indications falling into the largest of the three size thresholds are keyed red and/or with the numeral "1," that indications falling into the smallest of the three size thresholds are keyed purple and/or with the numeral "3," and/or that indications falling into the middle-sized of the three thresholds are keyed yellow and/or with the numeral "2."

Turning to keying which conveys AOI classification, indicators may identify classifications assigned to intraoral areas of interest. For examples, AOIs may be classified as voids, changes, conflicts, foreign objects, or other types of AOI. AOIs representing changes in patient dentition may represent tooth decay, receding gums, tooth wear, a broken tooth, gum disease, gum color, moles, lesions, tooth shade, tooth color, an improvement in orthodontic alignment, degradation in orthodontic alignment, and so on. Different criteria may be used for identifying each such class of AOI. For example, a void may be identified by lack of image data, a conflict may be identified by conflicting surfaces in image data, changes may be identified based on differences in image data, and so on.

In an example of a surface conflict AOI, a first bite line component may correspond to one portion of a patient's teeth (e.g., the upper jaw or to the right side of the jaw). A second bite line component may correspond to another portion of the patient's teeth (e.g., the lower jaw or to the left side of the jaw). The AOI identifying module 115 may compare the first bite line component to the second bite line component to check for a deviation. Such a deviation might be suggestive of the patient having moved his jaw during scanning (e.g., the patient having moved his jaw in an interim between a practitioner's scanning of the lower jaw and the practitioner's scanning of the upper jaw, or in an interim between the practitioner's scanning of the left side of the jaw and the and the practitioner's scanning of right side of the jaw).

In performing a bite line shift surface conflict operation, the AOI identifying module 115 may or may not take into account a deviation threshold (e.g., set during a configuration operation). The flagging module 118 may or may not then provide indication thereof in the case where the found deviation meets the threshold, and not provide indication otherwise. The intraoral scan application 108 may or may not apply corrective measures (e.g., averaging) to such found deviations which do not meet the threshold. Where such a threshold is not taken into account, the flagging module 118 may provide indication of all found deviations. Although the foregoing is, to facilitate discussion, cast in terms of bite line shift surface conflict, analogous operations may be performed, for instance, with regard to other surface conflict indications.

Keying may also include importance rank, which is discussed in greater detail with reference to FIG. 3B.

When a scan session is complete (e.g., all images for a dental site have been captured), model generation module 125 may generate a virtual 3D model of the scanned dental site. AOI identifying module 115 and/or flagging module 118 may perform operations to identify AOIs and/or to indicate such AOIs before or after a virtual 3D model has been generated.

To generate the virtual model, model generation module 125 may register (i.e., "stitch" together) the intraoral images generated from the intraoral scan session. In one embodiment, performing image registration includes capturing 3D data of various points of a surface in multiple images (views from a camera), and registering the images by computing transformations between the images. The images may then be integrated into a common reference frame by applying appropriate transformations to points of each registered image. In one embodiment, processing logic performs image registration in a manner discussed in U.S. Pat. No. 6,542,249, filed Jul. 20, 1999, which is incorporated herein by reference.

In one embodiment, image registration is performed for each pair of adjacent or overlapping intraoral images (e.g., each successive frame of an intraoral video). Image registration algorithms are carried out to register two adjacent intraoral images, which essentially involves determination of the transformations which align one image with the other. Each registration between a pair of images may be accurate to within 10-15 microns. Image registration may involve identifying multiple points in each image (e.g., point clouds) of an image pair, surface fitting to the points of each image, and using local searches around points to match points of the two adjacent images. For example, model generation module 125 may match points of one image with the closest points interpolated on the surface of the other image, and iteratively minimize the distance between matched points. Model generation module 125 may also find the best match of curvature features at points of one image with curvature features at points interpolated on the surface of the other image, without iteration. Model generation module 125 may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, model generation module 125 may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Model generation module 125 repeats image registration for all adjacent image pairs of a sequence of intraoral images to obtain a transformation between each pair of images, to register each image with the previous one. Model generation module 125 then integrates all images into a single virtual 3D model by applying the appropriate determined transformations to each of the images. Each transformation may include rotations about one to three axes and translations within one to three planes.

In one embodiment, intraoral scan application 108 includes a training module 120. The training module 120 may provide a user (e.g., a practitioner) with training guidance as to scanning technique, and/or may highlight scan assistance indications of the sort discussed hereinabove (e.g., ones corresponding to missing and/or flawed scan data) which have occurred in the past and/or have been reoccurring for that user.

The training module 120 may consider, relative to a training guidance data pool, scan data (e.g., 3D image point clouds) and/or one or more virtual 3D models arising from scanning performed by that user which led to scan assistance indications. The training guidance data pool may include, with respect to the scanning performances of multiple users (e.g., multiple practitioners), scan data and/or one or more virtual 3D models (e.g., one which led to scan assistance indications) along with information describing scanning technique changes which might have prevented and/or mitigated the circumstances which led to the scan assistance indications. The scan data and/or one or more virtual 3D models of the training guidance data pool may be anonymized and/or employed in compliance with regional medical record privacy regulations. The training module 120 may match the scan data and/or one or more virtual 3D models arising from scanning performed by the user to scan data and/or virtual 3D models of the training guidance data pool, access corresponding information describing scanning technique changes, and present such scanning change technique information to the user (e.g., via a user interface).

As an illustration, the training guidance data pool might, for scan data and/or one or more virtual 3D models which led to double incisor edge scan assistance indications such as ones corresponding to particular angles of scanning, include information indicating that having performed scanning with a specified angular change might have been preventative and/or mitigating. For instance, such data might, for scan data and/or one or more virtual 3D models which led to double incisor edge scan assistance indications in a fashion indicative of scanning at a 35 degree-to-surface angle—instead of a desired 45 degree-to-surface angle—include information indicating that an angular increase of ten degrees-to-surface might be preventative and/or curative. Moreover, such data might for scan data and/or one or more virtual 3D models which led to double incisor edge scan assistance indications in a fashion indicative of scanning with a 40 degree-to-surface angle—instead of the desired 45 degree-to-surface angle—include information indicating that an angular increase of five degrees-to-surface might be preventative and/or curative.

As another illustration, the training guidance data pool might, for scan data and/or one or more virtual 3D models which led to missing and/or flawed scan data scan assistance indications (e.g., ones corresponding to particular geometrical areas, width-height dimensions, width-to-height or other dimensional relationships, and/or oral locations), include information indicating that having performed scanning at one or more specified speeds, cadences, angles, and/or distances-from-surface might have been preventative and/or mitigating.

The training module 120 may with respect to particular users (e.g., practitioners) keep historical record (e.g., according to user identifier) of scan assistance indications over time. The training module 120 may employ this historical record to highlight scan assistance indications which have occurred in the past and/or have been reoccurring for a particular user, to identify improvements and/or declines in user scanning technique over time, and/or to provide scanning technique training guidance which takes into account multiple scanning performances of the user. The training module 120 may or may not consider the noted training guidance data pool information describing scanning technique changes which may be preventative and/or mitigating.

As one illustration, the training module 120 may in providing indication (e.g., flagging) regarding missing and/or flawed scan data recognize that a particular user has received same and or similar indication in the past. For instance, the training module 120 may ascertain that the user has received missing and/or flawed scan data at a given location multiple times, and/or has received missing and/or flawed scan data of similar tenor multiple times (e.g., although at differing locations, the user has repeatedly received indication reelecting double incisor edges suggestive of scanning at other than a 45-degrees-from-surface angle). Where the training module 120 so finds an at-hand indication to be one for which same and/or similar indication has been received in the past, the training module 120 may act to highlight the indication (e.g., via a particular color).

As another illustration, with respect to a particular user and double incisor edge scan assistance indications, the training module 120 may, by consideration of such historical record and such training guidance data pool scanning technique change information, ascertain that the user's scanning technique is changing in such a fashion that the employed scanning is not yet the called-for 45 degrees-to-surface, but that the employed scanning angle is becoming over time closer to 45 degrees-to-surface. In so doing the training module 120 may perform matching with training guidance data pool information in the vein of the noted differing degrees-to-surface scanning angles leading to double incisor edge scan assistance indication (e.g., matching older user data to pool data regarding 60-degree-to-surface scanning angle but more recent user data to pool data regarding 40-degree-to-surface scanning angle).

FIGS. 2A-3C illustrate flow diagrams of methods for performing intraoral scans of dental sites for patients. These methods may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing an intraoral scan application 108).

Figure 2A:
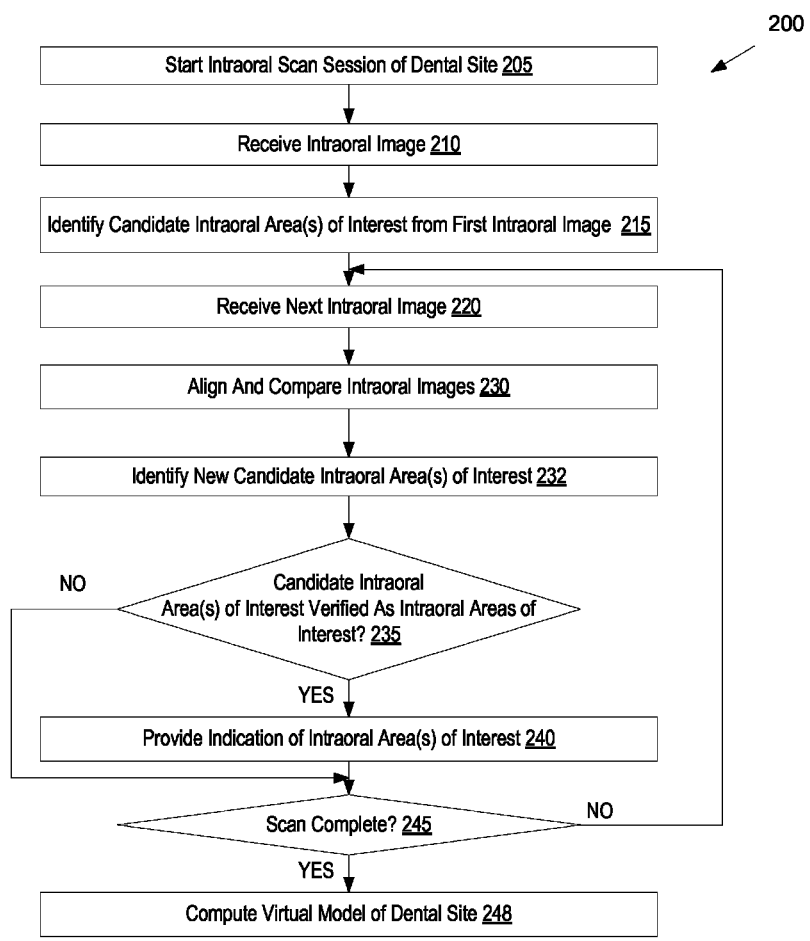
FIG. 2A illustrates a flow diagram for a method of determining intraoral areas of interest during an intraoral scan session, in accordance with embodiments of the present invention.

FIG. 2A illustrates a flow diagram for a method 200 of determining intraoral areas of interest during an intraoral scan session, in accordance with embodiments of the present invention. At block 205 of method 200, an intraoral scan session of a dental site is started by a dental practitioner. The scan session may be for an intraoral scan of a partial or full mandibular or maxillary arch, or a partial or full scan of both arches. The dental practitioner may move an intraoral scanner to a first intraoral position and generate a first intraoral image. At block 210, processing logic receives the first intraoral image. The first intraoral image may be a discrete image (e.g., taken from a point-and-shoot mode) or a frame of an intraoral video (e.g., taken in a continuous scanning or video mode). The intraoral image may be a three dimensional (3D) image having a particular height, width and depth. In some embodiments, an intraoral scanner is used that generates 3D images having a depth of 12-14 mm, a height of 13-15 mm and a width of 17-19 mm (e.g., a depth of 13 mm, height of 14 mm and width of 18 mm in one particular embodiment).

At block 215, processing logic identifies one or more candidate intraoral areas of interest from the first intraoral image. In one embodiment, a candidate intraoral area of interest is identified by processing the intraoral image to identify voxels in the intraoral image that satisfy one or more criteria. Different criteria may be used to identify different classes of intraoral areas of interest. In one embodiment, the a of missing image data is used to identify AOIs that might be voids. For example, voxels at areas that were not captured by the intraoral image may be identified.

Processing logic may then determine one or more subsets of the identified voxels that are proximate to one another. Two voxels may be considered to be proximate to one another if they are within a threshold distance from one another. In one embodiment, two voxels are proximate if they are adjacent to one another. All of the voxels in a determined subset (e.g., all of the voxels that are connected directly or via other identified voxels) are grouped into a volume that makes up the candidate area of interest. One or multiple candidate areas of interest may be identified. If the criterion used to identify voxels is a missing data, then the candidate intraoral area of interest may represent a void. Other criteria may be used to identify other classes of AOI.

After the dental practitioner generates the first intraoral image, he or she moves the intraoral scanner to a second position and generates a next intraoral image. At block 220, processing logic receives the next intraoral image. At block 230, processing logic compares the second intraoral image to the first intraoral image. To compare intraoral images, processing logic determines an alignment between the intraoral images based on geometric features shared by these intraoral images. Determining the alignment may include performing transformations and/or rotations on one or both of the intraoral images and/or register the intraoral areas of interest to each other. The aligned images may then be displayed by the processing logic. Processing logic may also compare the first intraoral image to a corresponding intraoral image taken during a prior scan session. This may identify areas of interest such as tooth wear, cavities, and so forth.

At block 232, processing logic determines whether any new candidate intraoral areas of interest are present based on the next intraoral image. At block 235, processing logic determines whether the candidate intraoral areas of interest from the first intraoral image are verified as intraoral areas of interest. Such verification may be performed by testing the proximity and/or geometric conditions of the AOI relative to a surface of the latest intraoral image. In one embodiment, candidate intraoral areas of interest from an intraoral image are dismissed if they correspond to a surface (e.g., of a dental site) from another intraoral image. Alternatively, if a candidate intraoral area of interest does not correspond to a region of a surface from another intraoral image, then the candidate intraoral image may be verified as an actual intraoral area of interest. Accordingly, the second intraoral image may be used to confirm or dismiss candidate intraoral areas of interest from the first intraoral image. If a portion of a candidate intraoral area of interest from the first intraoral image corresponds to (e.g., lines up with) a portion of a surface from the second intraoral image, then the shape and/or size of the candidate intraoral area of interest may be modified. If none of the candidate intraoral areas of interest are verified as intraoral areas of interest (e.g., if a subsequent intraoral image provides image data for a candidate intraoral area of interest), the method proceeds to block 245. Otherwise, the method continues to block 240.

At block 240, processing logic provides an indication of the one or more verified intraoral areas of interest. In one embodiment, processing logic interpolates a shape for the intraoral area of interest based on geometric features surrounding the intraoral area of interest and/or based on geometric features of the intraoral area of interest (if such features exist). For example, if the intraoral area of interest is a void, then the regions around the void may be used to interpolate a surface shape of the void. The shape of the intraoral area of interest may be displayed in manner to contrast the intraoral area of interest from surrounding imagery. For example, teeth may be shown in white, while the intraoral area of interest may be shown in red, black, blue, green, or another color. Additionally or alternatively, an indicator such as a flag may be used as an indication of the intraoral area of interest. The indicator may be remote from the intraoral area of interest but include a pointer to the intraoral area of interest. The intraoral area of interest may be hidden or occluded in many views of the dental site. However, the indicator may be visible in all or many such views. For example, the indicator may be visible in all views of the scanned dental site unless the indicator is disabled. The provided indications of the intraoral areas of interest may be displayed while the intraoral scan session is ongoing.

At block 245, processing logic determines whether the intraoral scan session is complete. If so, the method continues to block 248. If additional intraoral images are to be taken and processed, the method returns to block 220.

At block 248, a virtual 3D model of the dental site is generated. The virtual model 3D may be generated as discussed above. The virtual 3D model may be a virtual or digital model showing the surface features of the target area. For a virtual 3D model of a full dental arch, the arch width of the virtual 3D model may be accurate to within 200 microns of the arch width of the patient's actual dental arch.

Figure 2B:
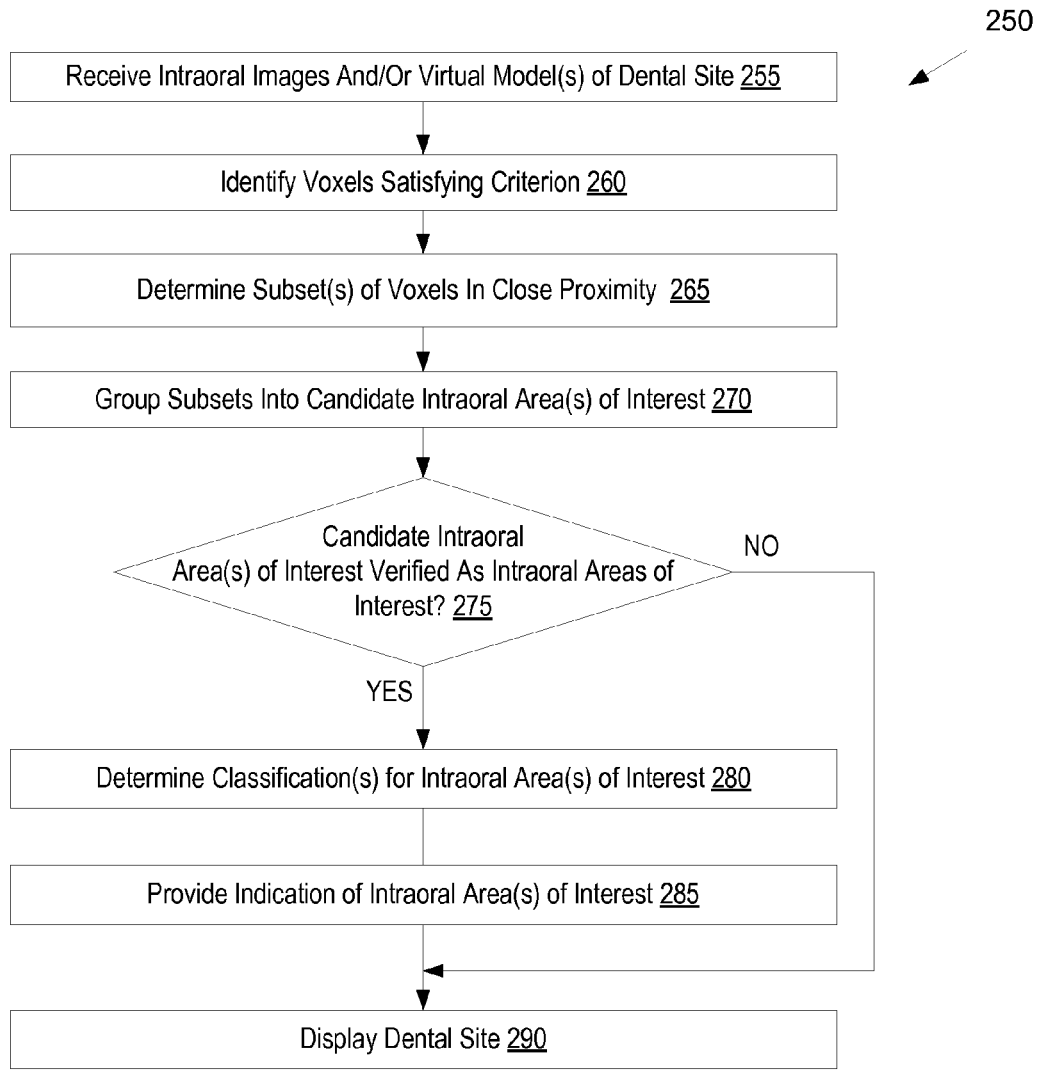
FIG. 2B illustrates a flow diagram for a method of providing indications for intraoral areas of interest, in accordance with embodiments of the present invention.

FIG. 2B illustrates a flow diagram for a method 250 of providing indications for intraoral areas of interest, in accordance with embodiments of the present invention. The indications may be provided during an intraoral scan session (e.g., before generation of a virtual model of a dental site) or after an intraoral scan session is complete (e.g., based on a virtual model of the dental site).

At block 255, intraoral images of a dental site are received. The intraoral images may be received from an intraoral scanner, from a data store, from another computing device, or from another source. The intraoral images may be from a single intraoral scan session or from multiple intraoral scan sessions. Additionally, or alternatively, one or more virtual models of a dental site may be received. The virtual models may have been computed based on intraoral images from past intraoral scan sessions.

At block 260, processing logic identifies one or more voxels from the intraoral images and/or the virtual models that satisfy a criterion. The criterion may be missing data, conflicting data, or data having particular characteristics. In one embodiment, the intraoral images are first used to compute a virtual model, and the voxels are identified from the computed virtual model. In another embodiment, the voxels are identified from individual intraoral images.

At block 265, one or more subsets of the identified voxels that are in close proximity to one another are identified. At block 270, these subsets are grouped into candidate intraoral areas of interest.

At block 275, processing logic determines whether the candidate intraoral areas of interest are verified as intraoral areas of interest. If any candidate intraoral areas of interest are verified as actual intraoral areas of interest, the method continues to block 280. Otherwise, the method proceeds to block 290.

At block 280, classifications are determined for the intraoral areas of interest. For example, AOIs may be classified as voids, conflicting surfaces, changes in a dental site, foreign objects, and so forth.

At block 285, processing logic provides indications of the intraoral areas of interest. The indications may include information identifying the determined classifications of the intraoral areas of interest. For example, an indicator may identify an intraoral area of interest as representing a void or insufficient image data. Another indicator may identify an intraoral area of interest as representing a region for which there are conflicting surfaces from different images.

In one embodiment, the indications include flags that are remote from the intraoral areas of interest and that point to or otherwise direct a viewer's attention to the intraoral areas of interest. The indications may be visible from views of the dental site at which the actual intraoral areas of interest are hidden. At block 290, the dental site is displayed along with any of the indications for the intraoral areas of interest.

Figure 3A:
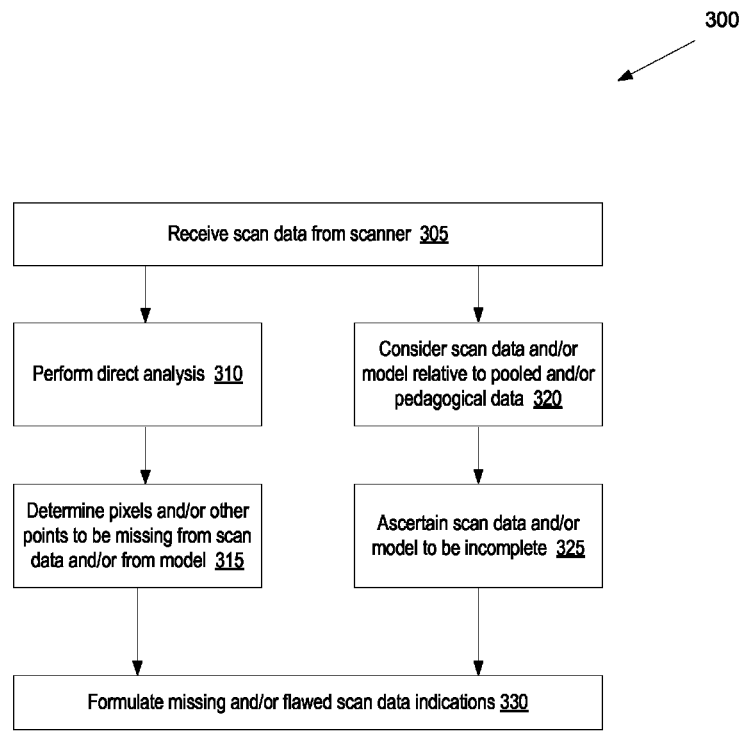
FIG. 3A illustrates a flow diagram for a method of providing data indications of flawed scan data from an intraoral scan session, in accordance with embodiments of the present invention.

FIG. 3A illustrates a flow diagram for a method 300 of formulating scan assistance indications concerning missing and/or flawed scan data in accordance with examples of the present invention. According to a first aspect, at block 305 of method 300 the processing logic may receive scan data from an intraoral scanner. At block 310 the processing logic, may perform direct 3D point cloud analysis and/or direct virtual 3D model analysis. At block 315 the processing logic may determine one or more pixels and/or other points to be missing from patient scan data and/or from one or more patient virtual 3D models. At block 330, the processing logic may formulate one or more corresponding indications concerning missing and/or flawed scan data.

According to a second aspect of FIG. 3, at block 305 the processing logic may likewise receive scan data from the scanner. At block 320, the processing logic may consider patient scan data and/or one or more patient virtual 3D models relative to entities indicated by pooled patient data and/or by pedagogical patient data to constitute complete and/or un-flawed data.

At block 325, the processing logic may ascertain the patient scan data and/or one or more patient virtual 3D models to be incomplete. At block 330, the processing logic may likewise formulate one or more corresponding indications concerning missing and/or flawed scan data. The indications regarding diagnostic assistance provided by the processing logic may include indications concerning tooth occlusion contacts, bite relation, tooth breakage, tooth wear, gingival swelling, gingival recess, and/or caries. To facilitate understanding, examples of processing logic operations performed in connection with providing diagnostic assistance indications will now be discussed.

Figure 3B:
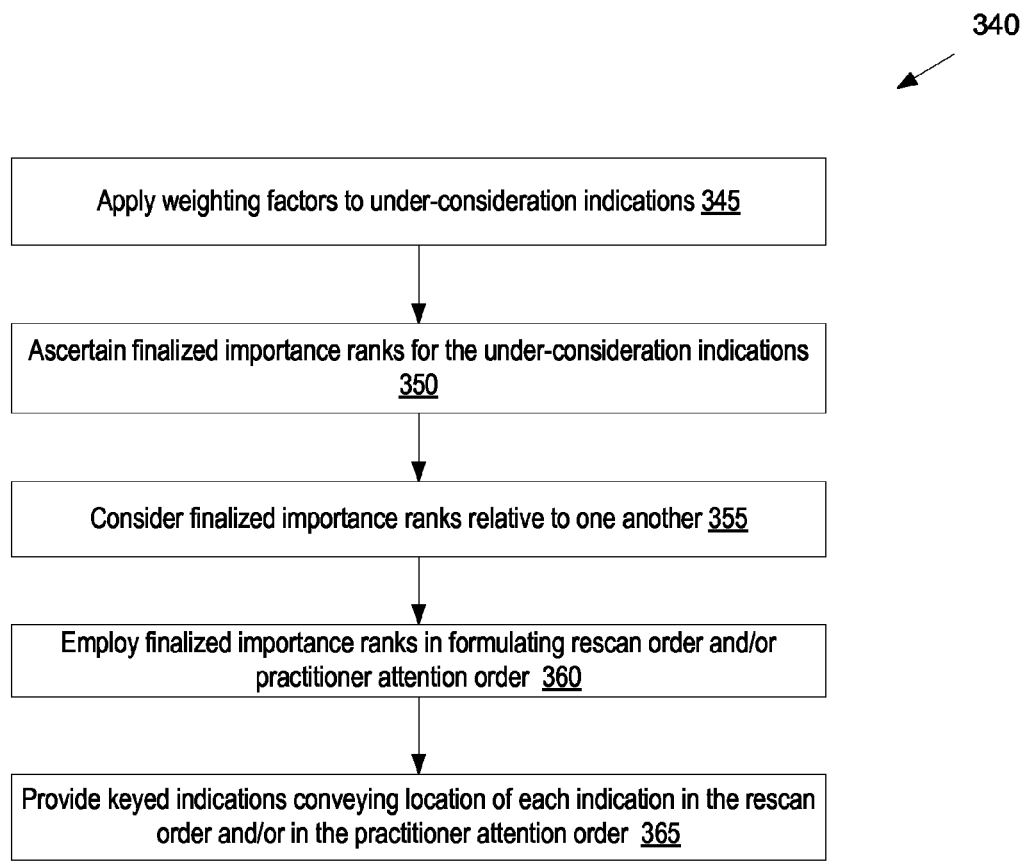
FIG. 3B illustrates a flow diagram for a method of providing data indications of intraoral areas of interest, in accordance with embodiments of the present invention.

FIG. 3B illustrates a flow diagram for a method 340 of performing keying and display which conveys indication importance rank for intraoral areas of interest in accordance with that which is discussed hereinabove and in connection with examples of the present invention. Processing logic may assign an importance rank to an indication via a process in which the processing logic considers the indication in view of one or more patient case details and/or one or more rank-altering weighting factors. It is noted that one or more of the rank-altering weighting factors themselves may or may not regard patient case details. Such patient case details may include a procedure being performed (e.g., preparation for application of a crown, preparation for application of an orthodontic alignment device, treatment of suspected caries and/or treatment of gingival swelling), patient age, patient gender, one or more previously-performed procedures (e.g., that a patient's last visit was to address a crown affected by marginal leakage), and/or patient dental records.

At block 345 of method 340 the processing logic may apply one or more weighting factors to each of the one or more under-consideration indications. A weighting factor may set forth one or more particular properties and indicate one or more rank alterations to be performed where such properties are met. The rank alterations may include increasing an indication's rank by a given value, decreasing an indication's rank by a given value, specifying that an indication be considered to possess a zenith rank, and/or that an indication be considered to possess a nadir rank. With respect to a given indication, the processing logic may commence by assigning a particular start rank value (e.g., zero) to the indication. The processing logic may then consider the one or more weighting factors. Having applied those weighting factors, the processing logic may ascertain a finalized importance rank for the indication. The processing logic may consider the finalized importance rank for the indication relative to one or more other indications for which it has performed like operations.

The origin of the rank-altering weighting factors considered by the processing logic may be set by processing logic which accesses pooled patient data and/or pedagogical patient data which includes correlations between foreseeable indications regarding diagnostic assistance (e.g., tooth wear and/or caries) and importance (e.g., the data might set forth importance information regarding each of tooth wear and caries that conveys that caries are of greater import than tooth wear).

Processing logic may set the rank-altering weighting factors such that missing and/or flawed scan data corresponding to a portion of teeth and/or gingivae that is larger than or equal to a certain size has an increased rank. Rank-altering weighting factors such as missing and/or flawed scan data which corresponds to a portion of teeth and/or gingivae which has certain dimensional characteristics (e.g., having width magnitude being greater than or equal to height magnitude, a circumstance that might be viewed as being short and wide or square shaped) are assigned the zenith rank or more highly ranked. Missing and/or flawed scan data which corresponds to a portion of teeth and/or gingivae which has other dimensional characteristics (e.g., having width magnitude being less than height magnitude, a circumstance that might be viewed as being long and narrow) may be assigned the nadir rank or more lowly ranked.

The origin of the rank-altering weighting factors considered by the processing logic may be set by processing logic which accesses pooled patient data and/or pedagogical patient data which includes correlations between foreseeable indications regarding foreign object recognition assistance (e.g., concerning fillings and/or implants) and importance (e.g., the data might set forth importance information regarding each of fillings and implants that conveys that fillings are of greater import than implants). By consideration of such data-provided correlations—be they ones regarding scan assistance, diagnostic assistance, or foreign object recognition assistance—the processing logic may draw conclusions which it employs in setting rank-altering weighting factors.

The performed setting—be it done during a configuration operation or by processing logic—may provide for one or more weighting factors directed towards foreseeable indications. One such weighting factor may specify that an indication relating to the vicinity of (e.g., to the interproximal areas of) one or more preparation teeth have its rank raised by a specified value. Another such weighting factor may specify that an indication regarding insufficient preparation tooth margin line clarity have its rank raised by a specified value or that such indication should possess a zenith rank. Yet another weighting factor may specify that an indication regarding unclear bite have its rank raised by a specified value. A further weighting factor may specify that an indication regarding bite line shift have its rank raised by a specified value. Another weighting factor may specify that an indication regarding double incisor edge have its rank raised by a specified value. Yet another weighting factor may specify that an indication regarding a lack of gum line clarity have its rank raised by a first specified value in the case where the at-hand procedure does not concern gingival recess, but have its rank raised by a second specified value in the case where the at-hand procedure does concern gingival recess.

As one example, with respect to a first indication the processing logic may commence by assigning an importance rank of zero to the indication, determine that consideration of a first weighting factor finds indication that the indication's rank be raised by three, that consideration of a second weighting factor finds indication that the indication's rank be lowered by one, and that consideration of a third weighting factor finds indication that the indication's rank be raised by five. The processing logic may then ascertain the finalized importance rank of the first indication to be seven.

Further, with respect to a second indication the processing logic may commence by assigning an importance rank of zero to the indication, determine that consideration of a first weighting factor finds indication that the indication's rank be lowered by two, that consideration of a second weighting factor finds indication that the indication's rank be lowered by three, and that consideration of a third weighting factor finds indication that the indication's rank be raised by six. The processing logic may then ascertain the finalized importance rank of the second indication to be one.

With respect to a third indication the processing logic may again commence by assigning an importance rank of zero. The processing logic may then find that consideration of a first weighting factor finds indication that the indication's rank be raised by four, that consideration of a second weighting factor finds indication that the indication be considered to possess a zenith rank, and that consideration of a third weighting factor finds indication that the indication's rank be lowered by eight. The processing logic may then ascertain the finalized importance rank of the third indication to be the zenith rank. As such, the second weighting factor, by indicating zenith rank, might be seen as having trumped that which was indicated by the other two weighting factors. It is noted that had consideration of the second weighting factor instead found indication that the indication be considered to possess a nadir rank, the second weighting factor would have again trumped the other two weighting factors, but would have done so in a fashion that yielded a finalized importance rank of the nadir rank for the third indication.

At block 350, the processing logic may ascertain a finalized importance rank for each of the one or more under-consideration indications. At block 355, the processing logic may consider relative to one another the finalized importance ranks of the one or more under-consideration indications. Continuing the above example, the processing logic may consider the three finalized importance ranks—seven for the first indication, one for the second indication, and zenith rank for the third indication—relative to one another. In so doing the processing logic may conclude the third indication to be highest-ranked, the first indication to be second-highest-ranked, and the second indication to be lowest-ranked.

At block 360, the processing logic may employ the finalized importance ranks in formulating a rescan order and/or a practitioner attention order. The processing logic may employ the importance ranks of indications in suggesting a rescan order for one or more indications (e.g., indications regarding scan assistance such as indications concerning missing and/or flawed scan data) and/or in suggesting a practitioner attention order for one or more indications (e.g., indications regarding diagnostic assistance and/or indications regarding foreign object recognition assistance). In formulating such rescan order and such practitioner attention orders the processing logic may or may not suppress one or more indications such that those indications are excluded from the rescan order or practitioner attention order. As one illustration, the processing logic may suppress indications having rank lower than a certain value (e.g., a value specified by the user and/or during a configuration). As another illustration, the processing logic may suppress indications having the nadir rank. Such suppression may serve to eliminate indications determined by the processing logic to lack clinical significance (e.g., with respect to an at-hand procedure—say preparation for application of a crown or an orthotic alignment device). As an illustration, suppressed indications may include missing and/or flawed scan data for which compensation can be performed (e.g., via the employ of extrapolation and/or generic data filling). The processing logic may—for those indications which have not been suppressed—convey importance rank via keying of indications (e.g., via color, symbol, icon, size, text, and/or number key).

Then, at block 365 the processing logic may provide in connection with a depiction of teeth and/or gingivae (e.g., a 3D image or a virtual 3D model) one or more keyed indications (e.g., flags) conveying for each indication its location in the rescan order and/or in the practitioner attention order. The processing logic may provide flags including numerals which each point to a particular portion of a depiction (e.g., a 3D image or a virtual 3D model) of teeth and/or gingivae of a patient and convey via the numeral the order-wise location of that oral portion.

As an illustration, suppose that there are four indications regarding scan assistance selectable by the processing logic for inclusion in a rescan order—an indication corresponding to teeth 15 and 16 (ISO 3950 notion), an indication corresponding to the gingiva of tooth 32 (ISO 3950 notation), an indication corresponding to teeth 18 and 17 (ISO 3950 notation), and an indication corresponding to tooth 44 (ISO 3950 notation). Then suppose that the indication correspond to teeth 18 and 17 has the nadir rank, and that the processing logic suppresses this indication, thereby eliminating it from the rescan order. Suppose further that the rescan order for the three remaining indications is such that the indication corresponding to the gingiva of tooth 32 has the highest importance rank of the remaining three and is first in the rescan order, that the indication corresponding to teeth 15 and 16 has the second highest importance rank of the remaining three and is second in the rescan order, and that the indication corresponding to tooth 44 has the lowest importance rank of the remaining three and is third in the rescan order. The provision of flags by the processing logic may be such that the indication corresponding to the gingiva of tooth 32 is flagged with a "1," the indication corresponding to teeth 15 and 16 is flagged with a "2," and the indication corresponding to tooth 48 is flagged with a "3."

As another illustration, suppose that there are three indications regarding diagnostic assistance—an indication corresponding to breakage of teeth 11 and 21 (ISO 3950 notation), an indication corresponding to bite relation, and an indication corresponding to gingival recess at the base of tooth 27 (ISO 3950 notation). Suppose further that the practitioner attention order is such that the indication corresponding to bite relation has the highest importance rank of the three and is first in the practitioner attention order, that the indication corresponding to the breakage has the second highest importance rank of the three and is second in the practitioner attention order, and that the indication corresponding to the gingival recess has the lowest importance rank of the three and is third in the practitioner attention order. The provision of flags by the processing logic may be such that the indication corresponding to bite relation is flagged with a "1," the indication corresponding to the breakage is flagged with a "2," and the indication corresponding to the gingival recess is flagged with a "3."

As an additional illustration, suppose that there are two indications regarding foreign object recognition assistance—an indication corresponding to a filling in tooth 16 (ISO 3950 notation) and an indication corresponding to a bridge at the expected anatomical location of teeth 35-37 (ISO 3950 notation). Suppose further that the practitioner attention order is such that the indication corresponding to the filling has the has the higher importance rank of the two and is first in the practitioner attention order, and that the indication corresponding to the bridge has the lower importance rank of the two and is second in the practitioner attention order. The provision of flags by the processing logic may be such that the indication corresponding to the filling is flagged with a "1" and the indication corresponding to the bridge is flagged with a "2."

Figure 3C:
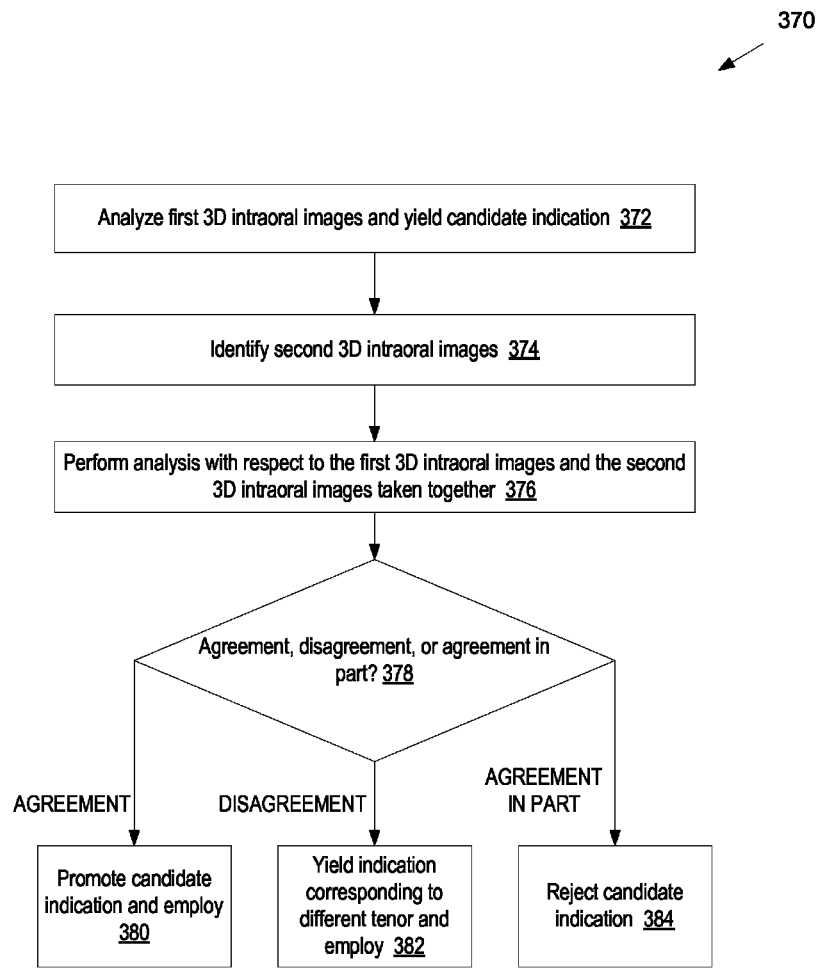
FIG. 3C illustrates a flow diagram for a method of performing intraoral scanning, in accordance with embodiments of the present invention.

FIG. 3C illustrates a flow diagram for a method 370 of employing 3D intraoral images in providing indication of intraoral areas of interest, in accordance with examples of the present invention. As discussed hereinabove, the processing logic may provide indication regarding scan assistance, diagnostic assistance, and/or foreign object recognition assistance. As also discussed hereinabove, the processing logic may provide such indication during the user's (e.g., the practitioner's) scanner application, after the user's scanner application, and/or prior to and/or without construction of an intraoral virtual 3D model. As additionally discussed hereinabove, in formulating such indication the processing logic may analyze intraoral scan data (e.g., 3D intraoral images, say 3D intraoral images provided by the scanner as 3D image point clouds) and/or intraoral virtual 3D models.

At block 372 of method 370 the processing logic may analyze one or more first 3D intraoral images to yield a candidate intraoral area of interest. The processing logic may perform such analysis as discussed hereinabove with respect to AOI formulation, but consider the analysis result to constitute a candidate intraoral area of interest rather than an actual intraoral area of interest. The processing logic may identify one or more points (e.g., one or more pixels and/or groups of pixels) corresponding to the candidate intraoral area of interest.

At block 374, the processing logic may identify one or more second 3D intraoral images which may be relevant to the candidate intraoral area of interest. The one or more second 3D intraoral images may be ones which are intraorally proximal to the first one or more 3D intraoral images and/or ones which share geometrical relation to the first one or more 3D intraoral images. The processing logic may determine such intraoral proximity by considering intraoral location information provided by the scanner in connection with 3D intraoral images. The scanner might produce such information by way of incorporated accelerometers and/or other positioning hardware. The processing logic may determine such shared geometrical relation by identifying common surface features (e.g., common peak and/or valley surface features).

At block 376, the processing logic may perform analysis with respect to one or more of the first 3D intraoral images and the second 3D intraoral images taken together. In so doing the processing logic may or may not align the one or more first 3D intraoral images with the one or more second 3D intraoral images (e.g., the processing logic may align one or more point clouds corresponding to the first one or more 3D intraoral images with one or more point clouds corresponding to the second one or more 3D intraoral images).

At block 378, the processing logic may determine whether the first 3D intraoral images and the second 3D intraoral images, taken together, agree, disagree, or agree in part with the candidate intraoral area of interest. As example, suppose that the candidate indication regards a scan assistance indication concerning missing and/or flawed scan data. In the case where such taken-together analysis finds no missing and/or flawed scan data disagreement may occur. As an illustration, such may occur where all of the one or more points (e.g., one or more pixels and/or groups of pixels) which correspond to missing scan data for the candidate indication are provided by the one or more second 3D intraoral images.

In the case where such taken-together analysis still finds missing and/or flawed scan data but the tenor of the missing and/or flawed scan data changes (e.g., the now-found missing and/or flawed scan data is of a larger size, of a smaller size, of a different location, and/or of a different morphology), partial agreement may occur. As an illustration, such might occur where some points (e.g., one or more pixels and/or groups of pixels) which correspond to missing scan data for the candidate indication are provided by the one or more second 3D intraoral images while other of such missing scan data points are not provided by the one or more second 3D intraoral images such that a smaller amount of missing and/or flawed scan data is found.

In the case where such taken-together analysis finds the same tenor (e.g., the same amount of) missing and/or flawed scan data, agreement may occur. As an illustration, such might occur where none of the points (e.g., one or more pixels and/or groups of pixels) which correspond to missing scan data for the candidate indication are provided by the one or more second 3D intraoral images.

As another example, suppose that the candidate indication regards a diagnostic assistance indication concerning caries. In the case where such taken-together analysis no longer finds caries disagreement may occur. As an illustration, such may occur where further taking into account the one or more second 3D intraoral images—say further taking into account one or more points (e.g., one or more pixels and/or groups of pixels) provided by the one or more second 3D intraoral images—yields a refined intraoral vantage point from which caries are no longer found.

In the case where such taken-together analysis still finds caries but the tenor of the found caries changes (e.g., the now-found caries are smaller, larger, of different location, and/or of different morphology), partial agreement may occur. As an illustration, such might occur where further taking into account the one or more second 3D intraoral images—say further taking into account one or more points (e.g., one or more pixels and/or groups of pixels) provided by the one or more second 3D intraoral images—yields a refined intraoral vantage point from which the found caries differ in size and/or intraoral location.

In the case where such taken-together analysis finds caries of the same tenor as that found in connection with the candidate indication agreement may occur. As an illustration, such might occur where further taking into account the one or more second 3D intraoral images—say further taking into account one or more points (e.g., one or more pixels and/or groups of pixels) provided by the one or more second 3D intraoral images—yields does not refine the intraoral vantage point in a way that causes the found caries to differ in size and/or in intraoral location.

Where the processing logic finds agreement, the processing logic may promote the candidate AOI to an indication of the sort discussed hereinabove (i.e., a full, non-candidate AOI) and employ it as discussed hereinabove (e.g., provide an indication of the AOI to a user in the form of flags). Where the processing logic finds partial agreement, the processing logic may yield an AOI corresponding to the above-discussed different tenor (e.g., an AOI reflecting a smaller amount of missing data or an AOI reflecting a caries of different morphology) and employ it as discussed hereinabove. Where the processing logic finds disagreement, the processing logic may reject the candidate AOI.

Where there is agreement the processing logic may proceed to block 380, in which the processing logic promotes the candidate indication to a full, non-candidate indication and employs the promoted indication as discussed above. Where there is partial agreement the processing logic may proceed to block 382, in which the processing logic yields an indication corresponding to the tenor of the partial agreement, and employs that indication as discussed above. Where there is disagreement the processing logic may proceed to block 384, in which the processing rejects the candidate indication.

Previously discussed pooled patient data and/or pedagogical patient data may include many different types of data and/or depictions. Some examples of different pooled patient data and/or pedagogical patient data and its use is now discussed.

Pooled patient data and/or pedagogical patient data may include depictions of gum lines, bites, and/or bite lines, along with corresponding identifications thereof and/or clarity level indications thereof. Indication regarding unclear gum line and/or unclear patient bite may involve the processing logic employing pooled patient data and/or pedagogical patient data to recognize that patient scan data and/or virtual 3D models includes a gum line or bite that is unclearly imaged (e.g., deviates, in a fashion suggestive of unclarity, from gum line or bite indicated by the pooled and/or pedagogical data to possess clarity.

Pooled patient data and/or pedagogical patient data may additionally include depictions of margin lines, tooth stumps, and/or accumulations (e.g., blood and/or saliva accumulations) along with corresponding identifications thereof. Indication regarding unclear margin line may involve the processing logic employing pooled patient data and/or pedagogical patient data to recognize that patient scan data and/or a virtual 3D model constitute a margin line (e.g., an upper portion of a tooth stump which is to receive prosthetic crown). Additionally, or alternatively, the processing logic may compare the margin line of under consideration patient scan data and/or one or more virtual 3D models of the patient to the margin line of an earlier-in-the-visit and/or dental record data to detect a margin line change suggestive of the buildup of blood, saliva, and/or like accumulation on the margin. The processing logic may consider found margin lines together with found blood, saliva, and/or like accumulation to locate instances of such accumulation appearing in the vicinity of such margin lines, and to conclude such instances to constitute unclear margin lines.

Pooled patient data and/or pedagogical patient data may include depictions of incisor edges and/or of double incisor edges along with corresponding identifications thereof. Indication regarding double incisor edge surface conflict may involve the processing logic employing pooled patient data and/or pedagogical patient data to recognize that patient scan data and/or virtual 3D models include one or more incisor edges, and further to conclude such incisor edges to deviate, in a fashion suggestive of double incisor edge, from incisor edges indicated by the pooled and/or pedagogical data to be proper incisor edges.

Pooled patient data and/or pedagogical patient data may include depictions of tooth occlusion contacts and/or bite relations along with corresponding identifications thereof. Indication regarding tooth occlusion contacts and/or bite relation may involve the processing logic employing pooled patient data and/or pedagogical patient data to recognize that patient scan data and/or virtual 3D models constitute tooth occlusion contacts and/or bite relation. The processing logic may further access one or more treatment goals (e.g., a desired degree of occlusion with respect to one or more indicated teeth and/or a desired bite relation). Such goals may be provided by a practitioner (e.g., via a user interface) and/or be retrieved from an accessible data store. The processing logic may then compare the tooth occlusion contacts and/or bite relation of the under consideration patient scan data and/or one or more virtual 3D models of the patient to the tooth occlusion contacts and/or bite relation of earlier-in-the-visit and/or dental record data to detect the degree of change (which might be null) of tooth occlusion contacts and/or bite relation. The processing logic may then compare the determined change to a treatment goal and ascertain whether the change causes satisfaction of the treatment goal, or whether the change serves to approach or depart the goal. The indication may include notification as to whether or not the change approaches, departs, meets the treatment goal, or results in no change relative to the treatment goal.

As one illustration, the aforementioned regarding tooth occlusion contacts may correspond to a circumstance in which a practitioner indicates a tooth occlusion contact treatment goal to the processing logic, has the processing logic receive scan data depicting a starting occlusion contact state of the patient, performs a dental procedure which serves to potentially alter that occlusion contact state, and that has the processing logic receive scan data depicting the post-procedure occlusion contact state. Via processing in vein of that which is discussed above, the practitioner may receive indication as to whether his procedure has met the treatment goal, caused progress towards the treatment goal, caused departure from the treatment goal, or resulted in no change relative to the treatment goal.

As another illustration, the aforementioned regarding bite relation may correspond to a circumstance in which a practitioner indicates a bite relation treatment goal to the processing logic, has the processing logic receive scan data depicting a starting bite relation state of the patient, applies an orthotic alignment device to the patient, and has the patient return at a later data. Then, at the later date, the practitioner has the processing logic receive scan data depicting the post-device-application bite relation state. Via processing in vein of that which is discussed above, the practitioner may receive indication as to whether his device application has caused the treatment goal to be met, caused progress towards the treatment goal, caused departure from the treatment goal, or has resulted in no change relative to the treatment goal.

Pooled patient data and/or pedagogical patient data may include depictions of tooth breakage, tooth wear, gingival swelling, gingival recess, and/or caries along with corresponding identifications thereof. Indication regarding tooth breakage, tooth wear, gingival swelling, gingival recess, and/or caries may involve the processing logic employing pooled patient data and/or pedagogical patient data to recognize that patient scan data and/or one or more virtual 3D models constitute tooth breakage, tooth wear, gingival swelling, gingival recess, and/or caries. For example, the processing logic may employ pooled patient data and/or pedagogical patient data to recognize teeth and/or gingiva in intraoral images and/or virtual 3D models. The processing logic may then compare the teeth and/or gingivae of the intraoral images and/or virtual 3D models to the teeth and/or gingivae of earlier intraoral images, virtual 3D models and/or dental record data to detect change indicative of tooth breakage, tooth wear, gingival swelling, gingival recess, and/or caries. In performing such detection the processing logic may or may not perform image analysis (e.g., considering a discovered change to be indicative of tooth breakage in the case where the change possesses a jagged edge) and/or consult patient data and/or pedagogical patient data (e.g., considering a discovered change to be indicative of tooth breakage in the case where the change matches one or more items indicated by the patient data and/or pedagogical patient data to constitute breakage).

Indication concerning tooth breakage and/or caries may involve the processing logic performing direct analysis. The processing logic may additionally or alternatively employ pooled patient data and/or pedagogical patient data to recognize that the patient scan data and/or one or more virtual 3D models includes areas that constitute teeth. The processing logic may determine (e.g., via edge recognition) one or more of such teeth to possess one or more jagged edges. The processing logic may consider such jagged edges to be indicative of tooth breakage. The processing logic may determine (e.g., via shape recognition) one or more of such teeth to possess spots and/or lacunae. The processing logic may consider such spots and/or lacunae to be indicative of caries.

The indications regarding foreign object recognition assistance provided by the processing logic may include indications concerning fillings, implants, and/or bridges. Pooled patient data and/or pedagogical patient data may include depictions of fillings, implants, and/or bridges along with corresponding identifications thereof. Indication regarding fillings, implants, and/or bridges may involve the processing logic employing pooled patient data and/or pedagogical patient data to recognize patient scan data and/or virtual 3D models which constitute fillings, implants, and/or bridges. Indication regarding fillings, implants, and/or bridges may involve the processing logic comparing the under consideration patient scan data and/or one or more virtual 3D models of the patient to earlier in the patient visit data, dental record data of the patient, and/or data of the patient from prior to the at-hand patient visit. The processing logic may consider objects which appear in the under consideration patient scan data and/or one or more virtual 3D models of the patient but not in the earlier in the patient visit data, dental record data of the patient, and/or data of the patient from prior to the at-hand patient visit to be possible foreign objects. Such functionality might, for instance, be implemented from the viewpoint that new objects appearing in a patient's mouth have a certain likelihood of being foreign objects rather than naturally-occurring ones. The processing logic may allow a practitioner to respond (e.g., via user interface) to such an indication with agreement and/or disagreement that processing logic-identified objects are foreign objects.

FIG. 4A illustrates an example scanned portion of a dental arch 400 during an intraoral scan session. The dental arch 400 includes gums 404 and multiple teeth 410, 420. Multiple intraoral images 425, 430, 435, 440 have been taken of a dental site of a patient. Each of the intraoral images 425-440 may have been generated by an intraoral scanner having a particular distance from the dental surface being imaged. At the particular distance, the intraoral images 425-440 have a particular scan area and scan depth. The shape and size of the scan area will generally depend on the scanner, and is herein represented by a rectangle. Each image may have its own reference coordinate system and origin. Each intraoral image may be generated by a scanner at a particular position (scanning station). The location and orientation of scanning stations may be selected such that together the intraoral images adequately cover an entire target zone. Preferably, scanning stations are selected such that there is overlap between the intraoral images 425-440 as shown. Typically, the selected scanning stations will differ when different scanners are used for the same target area, depending on the capture characteristics of the scanner used. Thus, a scanner capable of scanning a larger dental area with each scan (e.g., having a larger field of view) will use fewer scanning stations than a scanner that is only capable of capturing 3D data of a relatively smaller dental surface. Similarly, the number and disposition of scanning stations for a scanner having a rectangular scanning grid (and thus providing projected scanning areas in the form of corresponding rectangles) will typically be different from those for a scanner having a circular or triangular scanning grid (which would provide projected scanning areas in the form of corresponding circles or triangles, respectively).

Intraoral areas of interest 448 and 447 have been computed as discussed herein above. In the illustrated embodiment, the intraoral areas of interest 447, 448 represent portions of the patient's dental site that lack image data.

FIG. 4B illustrates a scanned portion of a dental arch 402 that is an update of dental arch 400. Additional intraoral images 458, 459 have been taken to provide image data corresponding to intraoral areas of interest 447, 448. Accordingly, intraoral areas of interest 447, 448 are no longer shown in dental arch 402. Additional intraoral images 460, 462, 464, 466 have also been generated. These additional intraoral images 460-466 reveal teeth 450, 452, 454, 456. New intraoral areas of interest 470, 472 are also determined based on the additional intraoral images 460-466. A practitioner may generate still further intraoral images to resolve intraoral areas of interest 470, 472 and to provide data for a full dental arch.

Figure 5A:
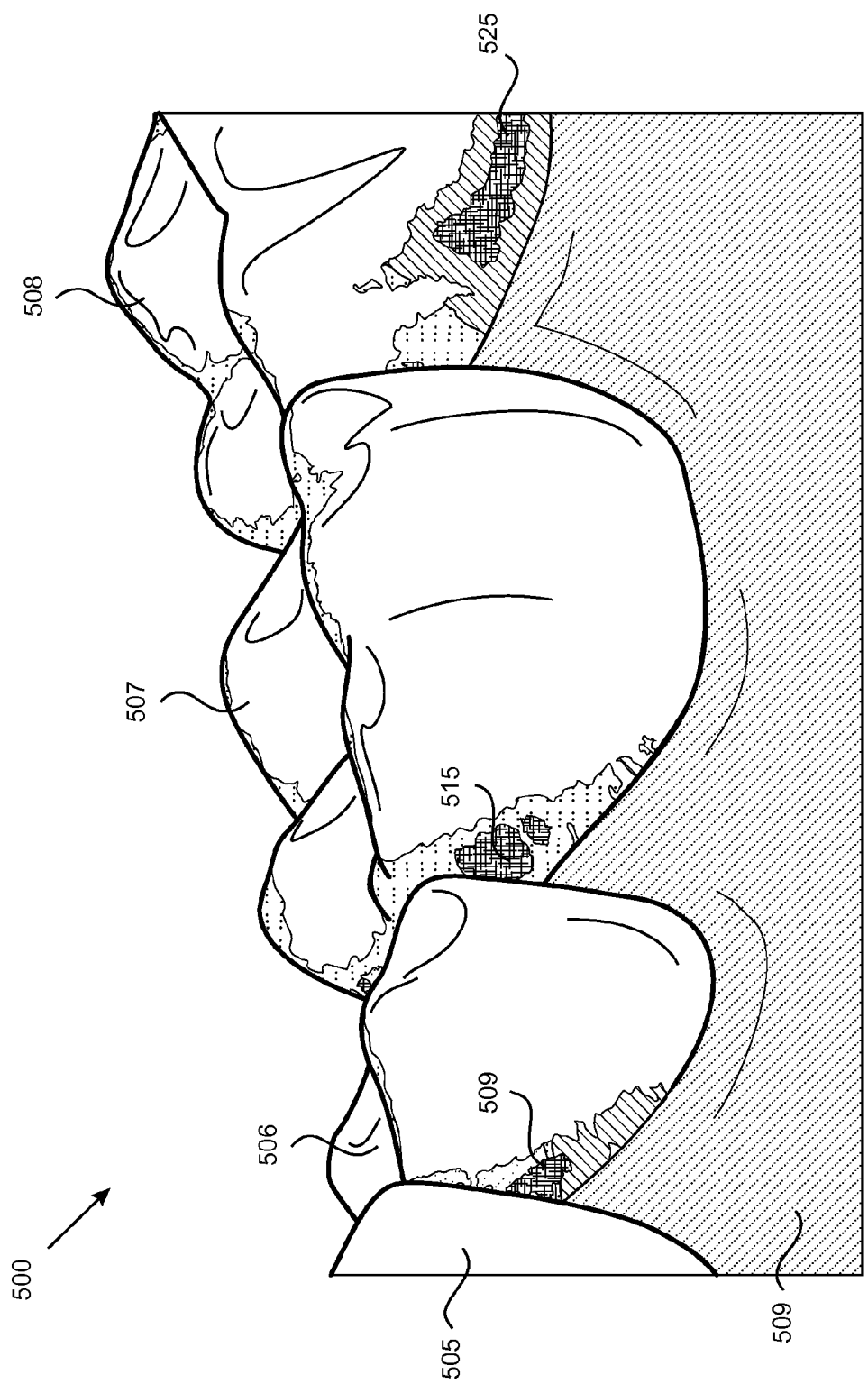
FIG. 5A illustrates an example dental arch showing intraoral areas of interest.

FIG. 5A illustrates an example image of a dental arch 500 showing areas of interest. The image of the dental arch 500 may be constructed from one or more intraoral scans prior to generation of a virtual 3D model. Alternatively, the image of the dental arch 500 may be constructed from one or more scans of a physical model of a dental arch. The image of the dental arch 500 includes gums 509 and multiple teeth 505-508. Multiple areas of interest 509, 515, 525 are also shown in the image of the dental arch 500. These areas of interest 509, 515, 525 represent missing scan data that satisfies a clinical importance criterion.

Figure 5B:
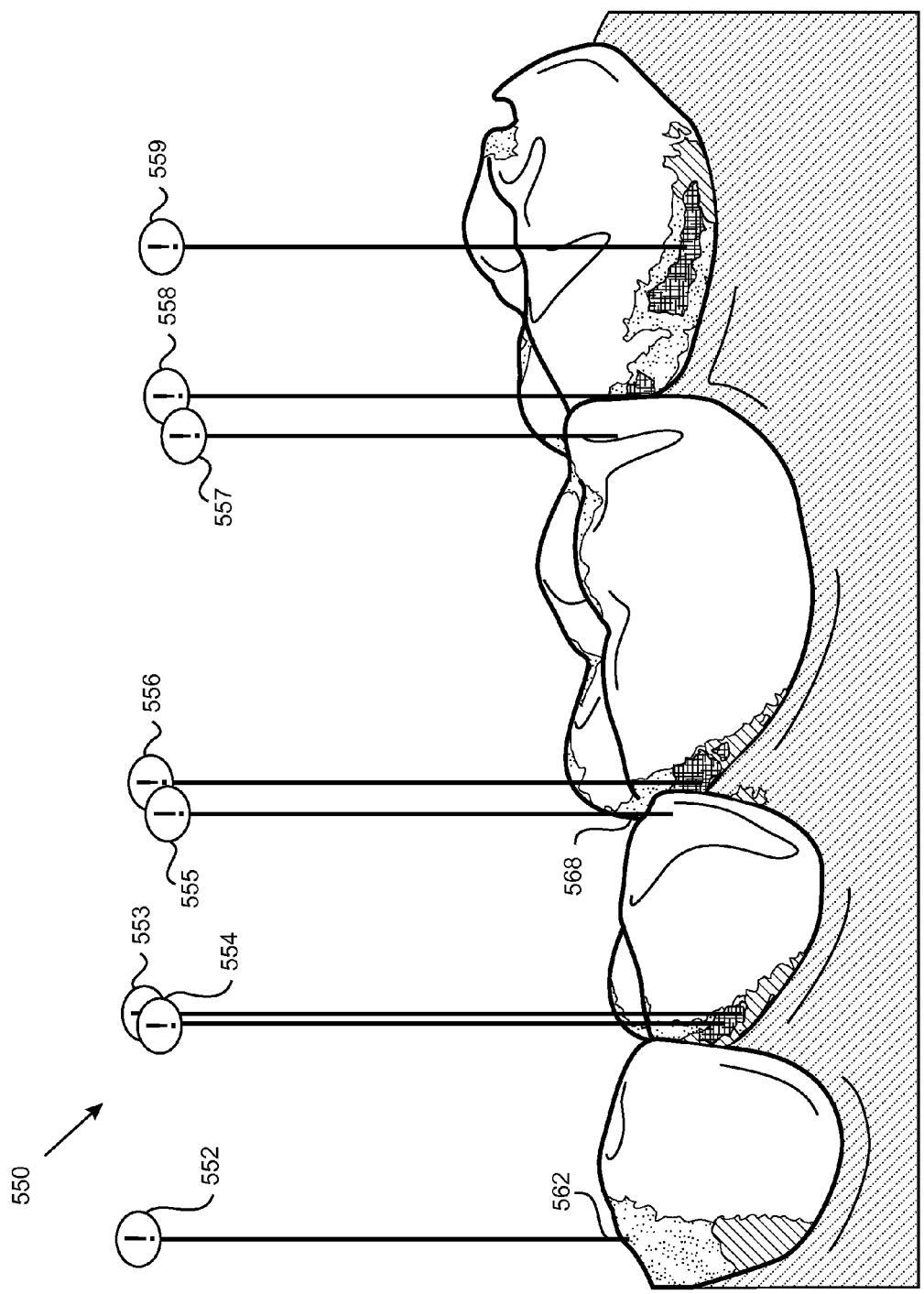
FIG. 5B illustrates an example dental arch showing intraoral areas of interest and indicators pointing to the intraoral areas of interest.

FIG. 5B illustrates an example image of a dental arch 550 showing areas of interest and indications pointing to the areas of interest. The image of the dental arch 550 may be constructed from one or more intraoral scans. Alternatively, the image of the dental arch 550 may be constructed from one or more scans of a physical model of a dental arch. The image of the dental arch 550 includes gums and multiple teeth. Multiple areas of interest 562, 564, 566, 568, 570, 572 are also shown in the image of the dental arch 550. These areas of interest 562, 564, 566, 568, 570, 572 represent missing scan data that satisfies a clinical importance criterion (e.g., intraoral areas of interest greater than a threshold size or having one or more dimensions that violate a geometric criterion). However, some areas of interest 562, 570 are largely occluded in the example image of the dental arch 550. Additionally, there are other areas of interest that are completely hidden. To ensure that a dental practitioner is made aware of such areas of interest, an indicator such as a flag is presented for each area of interest. For example, the image of the dental arch 550 includes flags 552-559. These flags call the dental practitioners attention to areas of interest that should be addressed regardless of a present view.

Figure 5C:
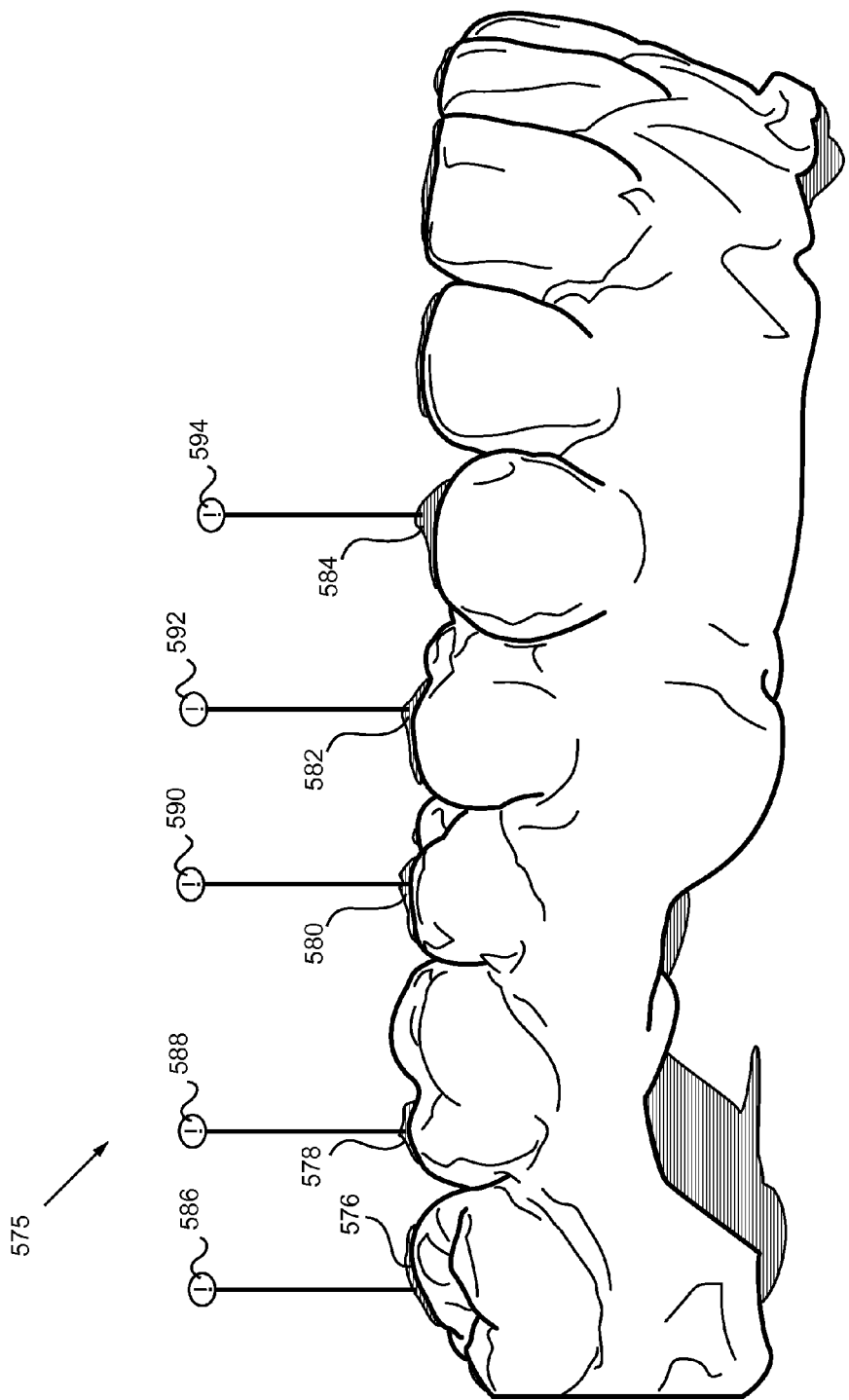
FIG. 5C illustrates another example dental arch showing intraoral areas of interest and indicators pointing to the intraoral areas of interest.

FIG. 5C illustrates another example image of a dental arch 575 showing areas of interest and indications pointing to the areas of interest. The image of the dental arch 575 may be constructed from one or more intraoral scans. Alternatively, the image of the dental arch 575 may be constructed from one or more scans of a physical model of a dental arch. The image of the dental arch 575 includes gums and multiple teeth. Multiple areas of interest 576-584 are also shown in the image of the dental arch 575. These areas of interest 576-584 represent tooth wear that is identified based on a comparison between images and/or a virtual 3D model generated at a first date and images and/or a virtual 3D model generated at a second date. However, some areas of interest 576, 578 are largely occluded in the example image of the dental arch 575. To ensure that a dental practitioner is made aware of such areas of interest, an indicator such as a flag is presented for each area of interest. For example, the image of the dental arch 575 includes flags 586-594. These flags call the dental practitioners attention to areas of interest that should be addressed regardless of a present view.

Figure 6:
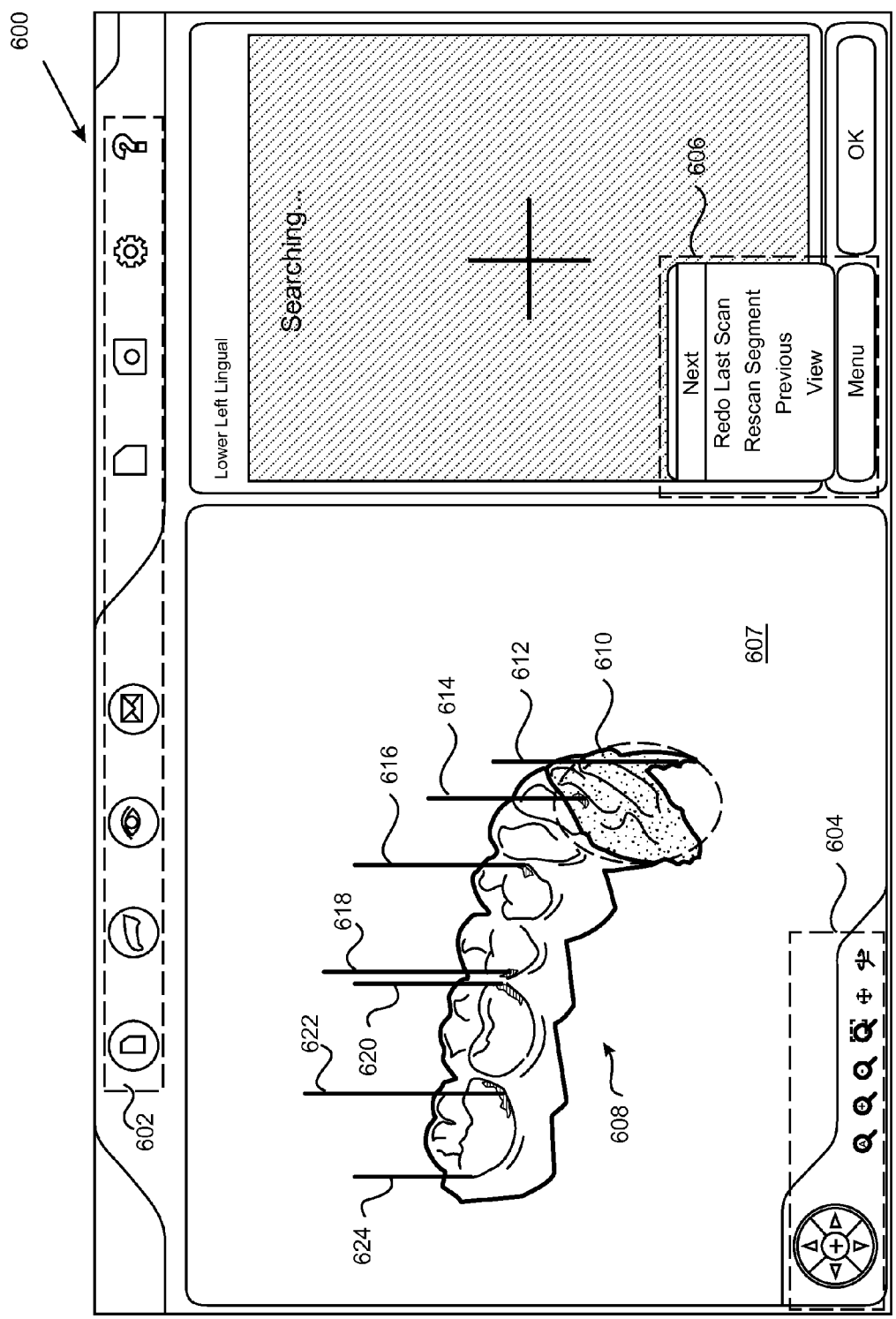
FIG. 6 illustrates a screen shot of an intraoral scan application, in accordance with embodiments of the present invention.

FIG. 6 illustrates a screen shot 600 of an intraoral scan application (e.g., of intraoral scan application 108 of FIG. 1), in accordance with embodiments of the present invention. The screen shot 600 shows multiple menus 602, 604, 606 for performing various operations. Menu 602 provides icons that can be selected to perform global operations such as changing settings, saving data, obtaining assistance, generating a virtual 3D model from gathered intraoral images, switching to a view mode, and so forth. Menu 604 provides icons for adjusting a view 607 of a scanned dental site 608. Menu 604 may include icons for panning, zooming, rotating, and so forth. The view 607 of the scanned dental site 608 includes a dental arch made up of one or more previous intraoral images that have been registered and/or aligned with one another. The view 607 further includes an indication of a latest intraoral image 610 that has been added to the dental arch.

The dental arch includes multiple voids based on incomplete scan data. Such voids are one type of intraoral area of interest that is called out by flags 612-624. Menu 606 includes scanning instructions that enable a user to proceed to a next scan, redo a last scan, rescan a segment, and so on. A user may rescan one or more segments to provide scan data that can fill in the voids that are called out by flags 612-624. This can ensure that a final virtual 3D model that is generated based on the intraoral images is of high quality.

Figure 7:
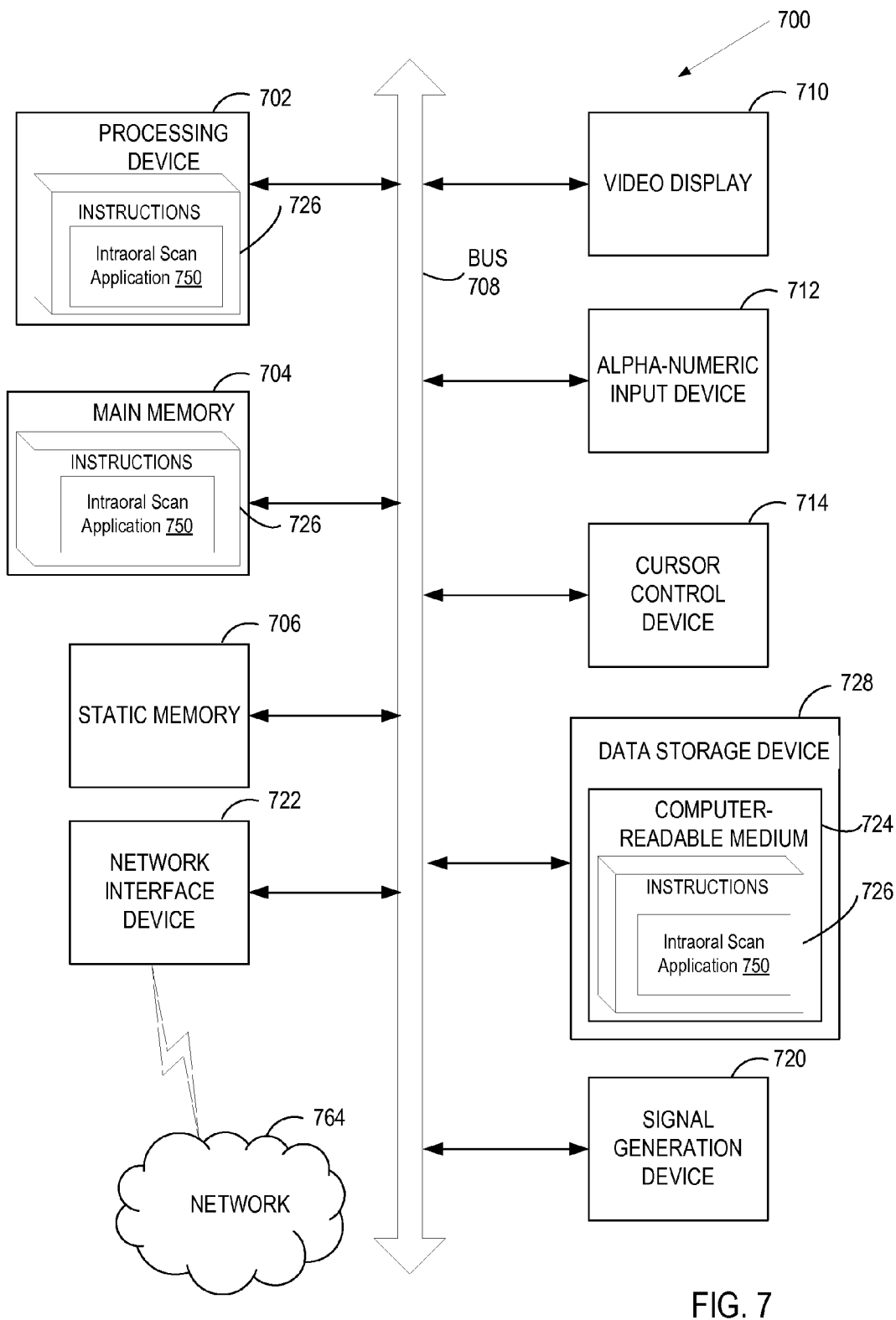
FIG. 7 illustrates a block diagram of an example computing device, in accordance with embodiments of the present invention.

FIG. 7 illustrates a diagrammatic representation of a machine in the example form of a computing device 700 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 700 includes a processing device 702, a main memory 704 (e.g., read-only memory (ROM), flash memory, dynamic random access memory (DRAM) such as synchronous DRAM (SDRAM), etc.), a static memory 706 (e.g., flash memory, static random access memory (SRAM), etc.), and a secondary memory (e.g., a data storage device 728), which communicate with each other via a bus 708.

Processing device 702 represents one or more general-purpose processors such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. Processing device 702 is configured to execute the processing logic (instructions 726) for performing operations and steps discussed herein.

The computing device 700 may further include a network interface device 722 for communicating with a network 764. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse), and a signal generation device 720 (e.g., a speaker).

The data storage device 728 may include a machine-readable storage medium (or more specifically a non-transitory computer-readable storage medium) 724 on which is stored one or more sets of instructions 726 embodying any one or more of the methodologies or functions described herein. A non-transitory storage medium refers to a storage medium other than a carrier wave. The instructions 726 may also reside, completely or at least partially, within the main memory 704 and/or within the processing device 702 during execution thereof by the computer device 700, the main memory 704 and the processing device 702 also constituting computer-readable storage media.

The computer-readable storage medium 724 may also be used to store an intraoral scan application 750, which may correspond to the similarly named component of FIG. 1. The computer readable storage medium 724 may also store a software library containing methods for an intraoral scan application 750. While the computer-readable storage medium 724 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A method comprising:
   receiving a first intraoral image of a dental site during an intraoral scan session;
   identifying, by a processing device, a first candidate intraoral area of interest from the first intraoral image;
   receiving a second intraoral image of the dental site during the intraoral scan session;
   verifying, by the processing device, the first candidate intraoral area of interest as an intraoral area of interest based on comparison of the second intraoral image to the first intraoral image; and
   providing, during the intraoral scan session, an indication of the intraoral area of interest.

2. The method of claim 1, wherein verifying the first candidate intraoral area of interest as an intraoral area of interest comprises:
   determining an alignment between the first intraoral image and the second intraoral image based on geometric features shared by the first intraoral image and the second intraoral image; and
   determining that the second intraoral image does not comprise a surface corresponding to the first candidate intraoral area of interest.

3. The method of claim 1, further comprising:
   identifying a second candidate intraoral area of interest from the first intraoral image;
   making a determination that the second candidate intraoral area of interest corresponds to a surface of the second intraoral image based on a comparison of the second intraoral image to the first intraoral image; and
   concluding that the second candidate intraoral area of interest is not an additional intraoral area of interest responsive to making the determination.

4. The method of claim 1, wherein identifying the first candidate area of interest comprises:
   identifying a plurality of voxels in the first intraoral image that satisfy a criterion;
   determining a subset of the plurality of voxels that are proximate to one another; and
   grouping the subset of the plurality of voxels into a volume that comprises the first candidate intraoral area of interest.

5. The method of claim 4, wherein the criterion comprises lack of image data and wherein the first candidate intraoral area of interest comprises a void in the first intraoral image.

6. The method of claim 5, further comprising:
   interpolating a shape for the void based on geometric features surrounding the void in at least one of the first intraoral image or the second intraoral image, wherein the indication of the intraoral area of interest comprises the shape of the void.

7. The method of claim 1, further comprising:
   computing a virtual model of the dental site after the intraoral scan session is complete based on a plurality of intraoral images, the plurality of intraoral images including the first intraoral image and the second intraoral image.

8. The method of claim 1, further comprising:
   receiving a new intraoral image comprising a region corresponding to the intraoral area of interest;
   determining an alignment between the new intraoral image and at least one of the first intraoral image or the second intraoral image;
   determining that the intraoral area of interest corresponds to a surface of the region in the new intraoral image; and
   removing the indication of the intraoral area of interest.

9. The method of claim 1, wherein the indication of the intraoral area of interest comprises a flag that points to the intraoral area of interest, wherein the intraoral area of interest is hidden in one or more views of the dental site, and wherein the flag is visible in the one or more views.

10. The method of claim 1, further comprising:
    providing feedback to a user of an intraoral scanner that generated the first intraoral image and the second intraoral image, wherein the feedback indicates a change in at least one of a motion of the intraoral scanner or a speed of the intraoral scanner that will improve a quality of the scan session.

11. The method of claim 1, wherein the intraoral area of interest comprises a conflicting surface between the first intraoral image and the second intraoral image.

12. The method of claim 1, wherein verifying the first candidate intraoral area of interest as an intraoral area of interest further comprises:

determining that the candidate intraoral area of interest has one or more dimensions that violate a geometric criterion.

13. A method comprising:

receiving a plurality of intraoral images of a dental site;

identifying, by a processing device and based on the plurality of intraoral images, a plurality of voxels satisfying a criterion;

determining a subset of the plurality of voxels that are proximate to one another;

grouping the subset of the plurality of voxels into an intraoral area of interest; and generating, by the processing device, an indication of the intraoral area of interest, wherein the intraoral area of interest is hidden in one or more views of the dental site, and wherein the indication of the intraoral area of interest is visible in the one or more views.

14. The method of claim 13, further comprising:

determining a classification for the intraoral area of interest;

determining at least one of a text, a color or an icon based on the classification; and presenting the classification for the intraoral image in the indication using at least one of the text, the color or the icon.

15. The method of claim 13, further comprising:

generating a first virtual model of the dental site based on a first scan session of the dental site taken at a first time;

generating a second virtual model of the dental site based on a second scan session of the dental site taken at a second time, wherein the plurality of intraoral images of the dental site are associated with the second scan session; and determining a change to the dental site based on a comparison of the second virtual model to the first virtual model, wherein the intraoral area of interest comprises the change.

16. The method of claim 15, wherein the change comprises at least one of tooth decay, receding gums, tooth wear, a broken tooth, gum disease, gum color, moles, lesions, tooth shade, tooth color, an improvement in orthodontic alignment or degradation in orthodontic alignment.

17. The method of claim 13, further comprising:

generating a virtual model of the dental site based on the plurality of intraoral images, wherein the intraoral area of interest is determined from the virtual model.

18. The method of claim 13, further comprising:

determining an alignment of two or more intraoral images of the plurality of intraoral images without generation of a virtual model; and identifying the intraoral area of interest based on a comparison of the two or more intraoral images.

19. The method of claim 13, wherein grouping the subset of the plurality of voxels into the intraoral area of interest comprises:

grouping the plurality of voxels into a candidate intraoral area of interest;

determining whether the candidate intraoral area of interest has clinical importance based on a geometry of the candidate intraoral area of interest; and responsive to determining that the candidate intraoral area of interest does has clinical importance, verifying the candidate intraoral area of interest as the intraoral area of interest.

20. The method of claim 13, wherein the intraoral area of interest comprises at least one of an intraoral area to be rescanned, an intraoral area suggestive of a dental lesion, an intraoral area suggestive of dental improvement, an intraoral area suggestive of dental deterioration, or an intraoral area suggestive of a foreign object.

21. The method of claim 13, wherein the indication of the intraoral area of interest comprises at least one of a rescan sequence, a clinical importance, or a size.

* * * * *

UNITED STATES PATENT AND TRADEMARK OFFICE
CERTIFICATE OF CORRECTION

PATENT NO. : 9,510,757 B2　　　　　　　　　　　　　　　　　　　　　　　　　Page 1 of 1
APPLICATION NO. : 14/705788
DATED : December 6, 2016
INVENTOR(S) : Avi Kopelman et al.

It is certified that error appears in the above-identified patent and that said Letters Patent is hereby corrected as shown below:

In the Claims

In Claim 19, Column 30, Line 25, delete "has" and insert --have--

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*